(12) United States Patent
Nilsson et al.

(10) Patent No.: US 10,983,676 B2
(45) Date of Patent: Apr. 20, 2021

(54) NORMAL WORKFLOW AND DEVIATIONS THEREFROM

(71) Applicant: GAMBRO LUNDIA AB, Lund (SE)

(72) Inventors: Roger Nilsson, Hoor (SE); Par-Olof Hakansson, Vellinge (SE); Bendik Torvin, Schaanwald (LI)

(73) Assignee: Gambro Lundia AB, Lund (SE)

( * ) Notice: Subject to any disclaimer, the term of this patent is extended or adjusted under 35 U.S.C. 154(b) by 0 days.

(21) Appl. No.: 16/464,961

(22) PCT Filed: Nov. 22, 2017

(86) PCT No.: PCT/EP2017/080061
§ 371 (c)(1),
(2) Date: May 29, 2019

(87) PCT Pub. No.: WO2018/099784
PCT Pub. Date: Jun. 7, 2018

(65) Prior Publication Data
US 2019/0332233 A1    Oct. 31, 2019

(30) Foreign Application Priority Data
Nov. 29, 2016   (SE) .................... 1651567-8

(51) Int. Cl.
*G06F 3/0484*     (2013.01)
*G16H 40/63*     (2018.01)
(Continued)

(52) U.S. Cl.
CPC ........... *G06F 3/0484* (2013.01); *A61M 1/282* (2014.02); *A61M 1/3403* (2014.02);
(Continued)

(58) Field of Classification Search
CPC .... H02M 7/521; H02M 7/7575; A61M 1/282; G06F 3/0482; G06F 3/0484; G06F 3/04817
See application file for complete search history.

(56) References Cited

U.S. PATENT DOCUMENTS 5,795,317  A  *  8/1998  Brierton .............. A61M 1/3624
                                                              604/6.05
2005/0070837 A1    3/2005  Ferranini
(Continued)

FOREIGN PATENT DOCUMENTS

EP        1668556        2/2011
EP        2851832        3/2015
(Continued)

OTHER PUBLICATIONS

PCT Search Report and Written Opinion for PCT/EP2017/080061 dated Feb. 20, 2018 (11 pages).
(Continued)

*Primary Examiner* — Cao H Nguyen
(74) *Attorney, Agent, or Firm* — Mueting Raasch Group

(57) ABSTRACT

A normal workflow including a plurality of steps may be defined by exemplary systems and methods for use in preparing a treatment, performing a treatment, and performing post-treatment processes. A user may be guided by one or more workflow affordances to indicate where and how to use a graphical user interface to follow the normal workflow. When a user deviates from the normal workflow, one or more deviation workflow affordances may be displayed on the graphical user interface to guide a user back to the normal workflow.

33 Claims, 11 Drawing Sheets

(51) Int. Cl.
  G06F 3/0481   (2013.01)
  G06F 3/0482   (2013.01)
  A61M 1/28     (2006.01)
  A61M 1/34     (2006.01)
  G16H 20/40    (2018.01)

(52) U.S. Cl.
  CPC ........ *G06F 3/0482* (2013.01); *G06F 3/04817* (2013.01); *G16H 20/40* (2018.01); *G16H 40/63* (2018.01); *A61M 2205/505* (2013.01)

(56) References Cited

U.S. PATENT DOCUMENTS

| | | | | |
|---|---|---|---|---|
| 2012/0138533 A1* | 6/2012 | Curtis | ................. | A61M 1/1601 |
| | | | | 210/646 |
| 2015/0227293 A1 | 8/2015 | Stenquist | | |
| 2015/0347711 A1* | 12/2015 | Soli | ........................ | G16H 40/63 |
| | | | | 705/3 |
| 2019/0001039 A1* | 1/2019 | Heide | .................. | A61B 5/4836 |
| 2019/0301083 A1* | 10/2019 | Mor | ...................... | D06P 5/2077 |

FOREIGN PATENT DOCUMENTS

| | | |
|---|---|---|
| JP | 2015/062695 | 4/2015 |
| WO | WO 80/02376 | 11/1980 |
| WO | WO 2010/027437 | 3/2010 |
| WO | WO 2015/071265 | 5/2015 |
| WO | WO 2016/089753 | 11/2015 |
| WO | WO 2016/089741 | 6/2016 |
| WO | WO 2017/001559 | 1/2017 |

OTHER PUBLICATIONS

Bo Yu et al., "Building Dialysis Workflows into EMRs", *ScienceDirect*, Procedia Technology, vol. 9, Jan. 1, 2013, pp. 985-995.

\* cited by examiner

NORMAL WORKFLOW AND DEVIATIONS THEREFROM

This application is a U.S. National Stage Application of International Application No. PCT/EP2017/080061 filed 22 Nov. 2017 and published in English on 7 Jun. 2018 as International Publication No. WO 2018/099784 A1, which claims the benefit of priority under 35 U.S.C. § 119(a) of Swedish Patent Application No. 1651567-8 filed 29 Nov. 2016, each of which are incorporated herein by reference in their entireties.

The disclosure herein relates to medical treatment systems. More particularly, the disclosure relates to a normal workflow related to treatments performed by treatment systems and deviations from the normal workflow.

Medical treatment systems may define one or more steps, or processes, for performing particular medical treatments and other processes with respect to the medical treatment systems. For example, users may follow such steps to prepare a medical treatment, perform a medical treatment, and execute post-treatment tasks.

Medical treatment systems may be configured to perform extracorporeal blood treatment using extracorporeal blood treatment apparatus. Extracorporeal blood treatment may refer to taking blood from a patient, treating the blood outside the patient, and returning the treated blood to the patient. Extracorporeal blood treatment is typically used to extract undesirable matter or molecules from the patient's blood, and/or to add beneficial matter or molecules to the blood. Extracorporeal blood treatment may be used with patients incapable of effectively eliminating such undesirable matter from their blood, for example, in the case of a patient who is suffering from temporary or permanent kidney failure. These and other patients may, for instance, undergo extracorporeal blood treatment to add to or to eliminate matter from their blood, to maintain an acid-base balance, and/or to eliminate excess body fluids.

SUMMARY

The exemplary systems and methods may be described as overcoming usability barriers to performing many processes, or tasks, using treatment apparatus (e.g., extracorporeal blood treatment apparatus) and offering a user-friendly graphical user interface to assist users in performing such processes or tasks. For example, the exemplary systems and methods may be described as providing a normal workflow including a plurality of steps, which may defined at least in part by a prescription, for performing a treatment (e.g., an extracorporeal blood treatment). Further, the exemplary systems and methods may be described as providing a unique and user-friendly way on a graphical user interface to indicate, or suggest, the next step in the normal workflow (e.g., recommended next step in the normal, or standard, workflow) using workflow affordances. Additionally, when a user deviates from the normal workflow, the exemplary systems and methods may provide one or more workflow deviation affordances to indicate, or suggest, to a user how to return to the normal workflow. In other words, workflow affordances and workflow deviation affordances may be used to provide a recommended course of action to follow and/or return to a normal workflow to perform various tasks associated with the extracorporeal blood treatment systems. Further, the normal workflow including a plurality of steps, the workflow affordances, and the workflow deviation affordances, may be useful for the training of new users to use the system to prepare treatments, perform treatments, and execute post-treatment processes. Thus, the exemplary systems and methods may be described as a useful training tool.

It may be further described that the exemplary systems and methods may provide a graphical user interface that is easy to understand, intuitive to operate, and welcoming to users. Further, the exemplary systems and methods may be described as providing, or giving, users clear, consistent processes for performing a normal workflow and returning to such normal workflow when intentional or unintentional deviations may occur, which may reduce stress and improve patient safety and improve efficiency. The exemplary systems and methods may translate to a better, more efficient working environment for users, which may thereby provide a safer and better treatment experience for patients.

One exemplary treatment system (e.g., extracorporeal blood treatment systems, peritoneal dialysis systems, infusion pump systems, etc.) may include treatment apparatus including one or more pumps, one or more sensors, and one or more disposable elements and a display (e.g., a touchscreen) including a graphical user interface. The graphical user interface may be configured to display a plurality of process feature graphical elements related to preparing a treatment (e.g., an extracorporeal blood treatment), performing a treatment, and performing post-treatment processes (e.g., disinfecting the treatment apparatus). Each process feature graphical element of the plurality of process feature graphical elements may correspond to a different process feature of the treatment system. The exemplary treatment system may further include a computing apparatus including one or more processors and may be operatively coupled to the treatment apparatus and the display. The computing apparatus may be configured to display a plurality of process feature graphical elements on the graphical user interface to be used by a user to prepare a treatment, to perform a treatment, and to perform post-treatment processes (e.g., disinfection of the treatment apparatus), and define a normal workflow including a plurality of steps for the preparation of a treatment, the performance of the treatment, and the performance of post-treatment processes (e.g., disinfection of the treatment apparatus). The computing apparatus may be further configured to display one or more of a plurality of workflow affordances on the graphical user interface to indicate to a user which of and how the plurality of process feature graphical elements are to be used to perform the plurality of steps of the normal workflow and display a workflow deviation affordance on the graphical user interface in response to a user deviating from the normal workflow (e.g., in response to the user deviating from the normal workflow using the plurality of process feature graphical elements). The workflow deviation affordance may indicate which of and how the plurality of process feature graphical elements are to be used to return to the normal workflow.

One exemplary method for a treatment system (e.g., extracorporeal blood treatment system, peritoneal dialysis system, infusion pump system, etc.) may include providing treatment apparatus including one or more pumps, one or more sensors, and one or more disposable elements for use in performing a treatment and displaying a plurality of process feature graphical elements on a graphical user interface on a display (e.g., a touchscreen) to be used by a user to prepare a treatment (e.g., an extracorporeal blood treatment), to perform a treatment, and to perform post-treatment processes (e.g., disinfection of the apparatus). The exemplary method may further include defining a normal workflow including a plurality of steps for the preparation of a treatment, the performance of the treatment, and the performance of post-treatment processes (e.g., disinfection of the treatment apparatus), displaying one or more of a plurality of workflow affordances on the graphical user interface of the display to indicate to a user which of and how the plurality of process feature graphical elements are to be used to perform the plurality of steps of the normal workflow, and displaying a workflow deviation affordance on the graphical user interface in response to a user deviating from the normal workflow (e.g., in response to the user deviating from the normal workflow using the plurality of process feature graphical elements). The workflow deviation affordance may indicate which of and how the plurality of process feature graphical elements are to be used to return to the normal workflow.

In one or more embodiments, the computing apparatus may be further configured to execute or the method may further include removing the one or more of the plurality of workflow affordances from the graphical user interface in response to display of the workflow deviation affordance. In one or more embodiments, the normal workflow is at least partially defined by a prescription. The prescription may include one or more of sodium settings, bicarbonate settings, anticoagulation settings, time, treatment modality, and ultrafiltration volume.

In one or more embodiments, the computing apparatus may be further configured to execute or the method may further include displaying, after the display of workflow deviation affordance on the graphical user interface, an additional workflow deviation affordance on the graphical user interface in response to a user deviating further from the normal workflow using the plurality of process feature graphical elements. The additional workflow deviation affordance may indicate which of and how the plurality of process feature graphical elements are to be used to return to being on deviation away from the normal workflow. Further, the computing apparatus may be further configured to execute or the method may further include removing the workflow deviation affordance from the graphical user interface in response to display of the additional workflow deviation affordance.

In one or more embodiments, the computing apparatus may be further configured to execute or the method may further include displaying an exceptions graphical element to allow a user to deviate from the normal workflow and displaying one or more deviations graphical elements in response to selection of the exceptions graphical element, wherein the one or more deviations graphical elements are selectable to initiate a deviation from the normal workflow. The one or more deviation graphical elements to deviate from the normal workflow may include an end treatment graphical element to end an ongoing treatment when the treatment is being performed, an initiate disinfection graphical element to initiate disinfection of the treatment apparatus when a treatment is being prepared, and/or a new treatment graphical element to initiate the preparation of a treatment without disinfecting the treatment apparatus when post-treatment processes are being performed.

In one or more embodiments, the computing apparatus may be further configured to execute or the method may further include displaying a guide graphical element and displaying a guide area including information related to the next step of the plurality of steps of the normal workflow to be performed to continue the normal workflow in response to selection of the guide graphical element.

In one or more embodiments, the plurality of process feature graphical elements may include a blood process feature graphical element corresponding to a blood circuit of the treatment apparatus, a dialysate process feature graphical element corresponding to a dialysate circuit of the treatment apparatus, and an ultrafiltration process feature graphical element corresponding to one or more ultrafiltration processes. In one or more embodiments, the plurality of process feature graphical elements may include a patient process feature graphical element representative of the patient and connection of the patient to a blood circuit of the treatment apparatus. In one or more embodiments, the plurality of workflow affordances and the deviation workflow affordance may include a graphical animation to indicate a direction that a process feature graphical element is to be moved and/or selected.

The above summary of the present disclosure is not intended to describe each embodiment or every implementation thereof. Advantages, together with a more complete understanding of the present disclosure, will become apparent and appreciated by referring to the following detailed description and claims taken in conjunction with the accompanying drawings.

DETAILED DESCRIPTION OF EXEMPLARY EMBODIMENTS

Figure 1:
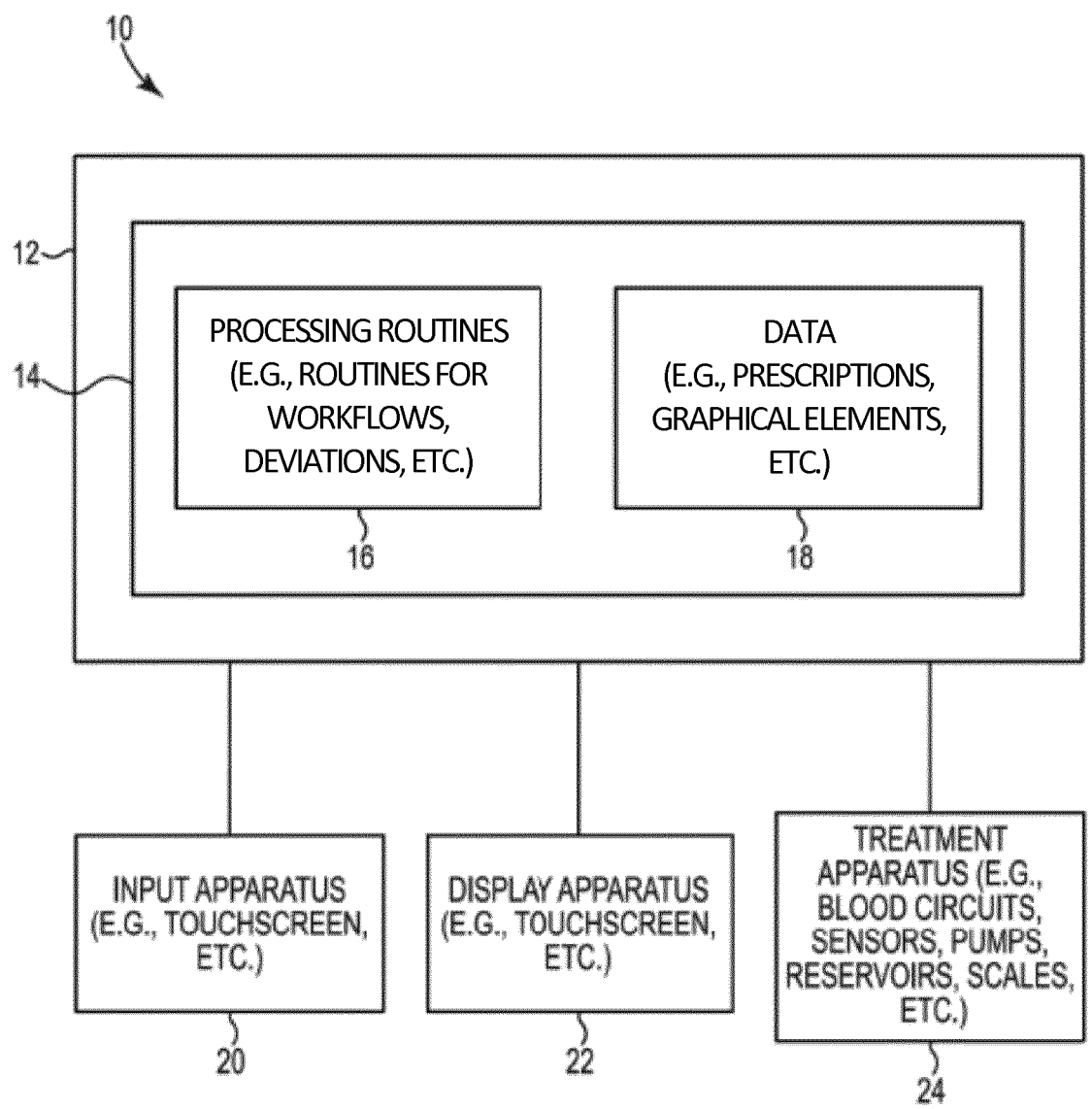
FIG. 1 is a block diagram of an exemplary medical treatment system including input apparatus, display apparatus, and treatment apparatus that may utilize the graphical user interfaces and methods described herein.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems, methods, and graphical user interfaces for use with medical treatment apparatus such as, e.g., extracorporeal blood treatment apparatus, peritoneal dialysis apparatus, infusion pump apparatus, etc. shall be described with reference to FIGS. 1-10. It will be apparent to one skilled in the art that elements or processes from one embodiment may be used in combination with elements or processes of the other embodiments, and that the possible embodiments of such systems, methods, and graphical user interfaces using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

The exemplary systems and methods may provide guidance to a user for the performance and execution of one or more tasks, or processes, according to a normal workflow, e.g., using an exemplary graphical user interface (e.g., user-interactable graphical user interface, graphical user interface depicted on single-touch or multi-touch touchscreens, etc.). The normal workflow may be based on at least a selected treatment and/or a selected prescription. In particular, the exemplary graphical user interface may include one or more workflow affordances configured to indicate to, or guide, users where and how to execute the one or more tasks to perform the normal workflow. Further, when a user deviates from, or leaves, the normal workflow, the exemplary graphical user interface may use one or more workflow deviation affordances to indicate to, or guide, users back to the normal workflow.

An exemplary extracorporeal blood treatment system 10 depicted in FIG. 1 may be used to execute, or perform, the methods and/or processes described herein. In at least one embodiment, the system 10 may be a machine for the extracorporeal treatment of blood. The system 10 could, for example, alternatively be a blood processing device or a blood component preparation device or other medical apparatus for fluid delivery/collection. Additionally, although FIG. 1 depicts an extracorporeal blood treatment system 10 and the remainder of the specification refers to an extracorporeal blood treatment system as an example, it is to be understood that the exemplary systems, methods, apparatus, and/or processes described herein may be used with any treatment systems such as, e.g., peritoneal dialysis systems, infusion pump therapy systems, etc.

As shown, the exemplary extracorporeal blood treatment system 10 includes computing apparatus 12. The computing apparatus 12 may be configured to receive input from input apparatus 20 and transmit output to display apparatus 22. Further, the computing apparatus 12 may include data storage 14. Data storage 14 may allow for access to processing programs or routines 16 and one or more other types of data 18 (e.g., prescriptions, normal workflows, deviation paths, return deviation paths, exceptions to normal workflows, treatment parameters, patient information, treatment information, graphical regions, graphical elements, graphical areas, graphical settings cards, metrics, variables, images, values, limits, text strings, macros, etc.) that may be employed to perform, or carry out, exemplary methods and/or processes (e.g., generating normal workflows, providing workflow affordances, providing workflow deviation affordances, providing guide areas, providing exceptions, displaying graphical user interfaces, allowing user interaction with graphical user interfaces, interpreting touch gestures on a touchscreen (e.g., swipes, drags, press-and-hold, touches, presses, etc.), displaying graphical elements, displaying textual elements, displaying textual values, running a treatment, determining problems with a treatment, exchanging/changing reservoirs, notifying operators/users of problems, etc.) for use in performing extracorporeal blood treatments. The computing apparatus 12 may be operatively coupled to the input apparatus 20 and the display apparatus 22 to, e.g., transmit data to and from each of the input apparatus 20 and the display apparatus 22. For example, the computing apparatus 12 may be operatively coupled to each of the input apparatus 20 and the display apparatus 22 using, e.g., analog electrical connections, digital electrical connections, wireless connections, bus-based connections, etc. As described further herein, an operator, or user, may provide input to the input apparatus 20 to manipulate, or modify, one or more graphical elements, graphical regions, and graphical areas displayed on the display apparatus 22 to, e.g., initiate one or more actions and/or processes related to the extracorporeal blood treatment system, indicate one or more actions and/or statuses related to one or more processes of the extracorporeal blood treatment system, etc.

Further, various devices and apparatus may be operatively coupled to the computing apparatus 12 to be used with the computing apparatus 12 to perform one or more extracorporeal procedures/treatments as well as the functionality, methods, and/or logic described herein. As shown, the system 10 may include input apparatus 20, display apparatus 22, and treatment apparatus 24 operatively coupled to the computing apparatus 12 (e.g., such that the computing apparatus 12 may be configured to use information, or data, from the apparatus 20, 22, 24 and provide information, or data, to the apparatus 20, 22, 24). The input apparatus 20 may include any apparatus capable of providing input to the computing apparatus 12 to perform the functionality, methods, and/or logic described herein.

For example, the input apparatus 20 may include a touchscreen (e.g., capacitive touchscreen, a resistive touchscreen, a multi-touch touchscreen, etc.), a mouse, a keyboard, a trackball, etc. A touchscreen may be part of (e.g., overlay) the display apparatus 22 such that, e.g., a user may use the touchscreen to interact (e.g., by touch) with a graphical user interface displayed on the display apparatus 22. For example, the input apparatus 20 may allow a user to interact with a graphical user interface including an operation region containing, or depicting, graphical elements, graphical regions, and graphical areas associated with and representative of (or corresponding to) one or more features or processes of the extracorporeal blood treatment system when used in conjunction with the display apparatus 22 (e.g., displaying the graphical user interface). Further, more specifically, the input apparatus 20 may allow a user to interact with a graphical user interface including a plurality of process feature graphical elements when used in conjunction with the display apparatus 22 (e.g., displaying the graphical user interface).

The display apparatus 22 may include any apparatus capable of displaying information to a user, such as a graphical user interface, etc., to perform the functionality, methods, and/or logic described herein. For example, the display apparatus 22 may include a liquid crystal display, an organic light-emitting diode screen, a touchscreen, a cathode ray tube display, etc. As described further herein, the display apparatus 22 may be configured to display a graphical user interface that includes one or more graphical regions, graphical elements, graphical areas, and/or affordances (e.g., process feature graphical elements, exception graphical regions, workflow affordances, workflow deviation affordances, etc.).

For example, the graphical user interface displayed by the display apparatus 22 may include, or display, an operation region that may include multiple graphical regions, graphical areas, and graphical elements related to the extracorporeal blood treatment system and/or for control of one or more processes during a treatment cycle (e.g., before treatment, during treatment, and after treatment). Such graphical regions, graphical areas, and graphical elements may include a plurality of process feature graphical elements that allow a user to perform one or more tasks, or processes, associated with the preparation of an extracorporeal blood treatment, the performance of an extracorporeal blood treatment, and/or the disinfection of extracorporeal blood treatment apparatus.

As used herein, a "region" of a graphical user interface may be defined as a portion of the graphical user interface within which information may be displayed or functionality may be performed and/or controlled by a user. Regions may exist within other regions, which may be displayed separately or simultaneously. For example, smaller regions may be located within larger regions, regions may be located side-by-side, etc. Additionally, as used herein, an "area" of a graphical user interface may be defined as a portion of the graphical user interface located within a region that is smaller than the region within which the area is located. Still further, as used herein, an "element" of a graphical user interface may be defined as a component of the graphical user interface that may be located within, or adjacent to, a region, an area, or another element. In one or more embodiments, an "element" of a graphical user interface may include a perimeter, or border, defining the outer edge, or boundary, of the element. In one or more embodiments, an "element" of a graphical user interface is a defined, finite portion, item, and/or section of a graphical user interface.

The processing programs or routines 16 may include programs or routines for performing normal workflow generation, workflow affordance generation, deviation affordance generation, exception generation, data recordation, computational mathematics, touchscreen gesture interpretation algorithms, process performance algorithms, process automation algorithms, matrix mathematics, standardization algorithms, comparison algorithms, or any other processing required to implement one or more exemplary methods and/or processes described herein. Data 18 may include, for example, normal workflows, prescriptions, deviations paths, exception paths, workflow affordances, deviation affordances, variables, graphics (e.g., graphical elements, graphical areas, graphical regions, affordance graphics and/or animations, icons, buttons, windows, dialogs, pull-down menus, 3D graphics, images, animations, etc.), graphical user interfaces, alarm data, fluid data, flow rates, fluid volumes, notifications, pressures, pressure limits, blood flow, blood flow limits, fluid removal rates, fluid removal limits, target blood temperatures, blood temperature limits, heuristics indicative of malfunction, results from one or more processing programs or routines employed according to the disclosure herein, or any other data that may be necessary for carrying out the one and/or more processes or methods described herein.

In one or more embodiments, the system 10 may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The program used to implement the methods and/or processes described herein may be provided using any programmable language, or code, e.g., a high level procedural and/or object orientated programming language or code that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the system 10 may be implemented using a computer readable storage medium, configured with a computer program, where the storage medium so configured causes the computer to operate in a specific and predefined manner to perform functions described herein. Further, in at least one embodiment, the system 10 may be described as being implemented by logic (e.g., object code) encoded in one or more non-transitory media that includes code for execution and, when executed by one or more processors, is operable to perform operations such as the methods, processes, and/or functionality described herein.

The computing apparatus 12 may be, for example, any fixed or mobile computer system (e.g., a controller, a microcontroller, a personal computer, mini computer, etc.). The exact configuration of the computing apparatus 12 is not limiting, and essentially any device capable of providing suitable computing capabilities and control capabilities (e.g., graphics processing, control of extracorporeal blood treatment apparatus, etc.) may be used.

As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 12 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

The methods and/or logic described in this disclosure, including those attributed to the systems, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems, devices and methods described in this disclosure may be embodied as instructions and/or logic on a computer-readable medium such as RAM, ROM, NVRAM, EEPROM, FLASH memory, magnetic data storage media, optical data storage media, or the like. The instructions and/or logic may be executed by one or more processors to support one or more aspects of the functionality described in this disclosure.

The treatment apparatus 24 may include any apparatus used by an exemplary extracorporeal blood treatment system capable of performing extracorporeal blood treatments, such as, e.g., blood circuits, sensors, pumps, reservoirs, scales, treatment sets, filters, pressure sensors, etc. For example, the treatment apparatus 24 may include one or more elements, or components, of the extracorporeal blood treatment system 100 described herein with reference to FIG. 2.

The exemplary systems, and exemplary methods performed, or used, by such exemplary systems, described herein may include systems such as, e.g., dialysis systems. The general term "dialysis" as used herein includes hemodialysis, hemofiltration, hemodiafiltration, hemoperfusion, liver dialysis, and therapeutic plasma exchange (TPE), among other similar treatment procedures. In dialysis generally, blood is taken out of the body via an arterial blood circuit and exposed to a treatment device to separate substances therefrom and/or to add substances thereto, and is then returned to the body via a venous blood circuit. Although extracorporeal blood treatment systems capable of performing general dialysis (as defined above, including TPE) shall be described herein with reference to the exemplary extracorporeal blood treatment system of FIG. 2, other systems such as those for infusion of drugs, performance of continuous renal replacement therapy (CRRT), extracorporeal membrane oxygenation (ECMO), hemoperfusion, liver dialysis, apheresis, TPE, etc. may benefit from the systems, methods, and apparatus described herein and the present disclosure is not limited to any particular treatment system.

Figure 2:
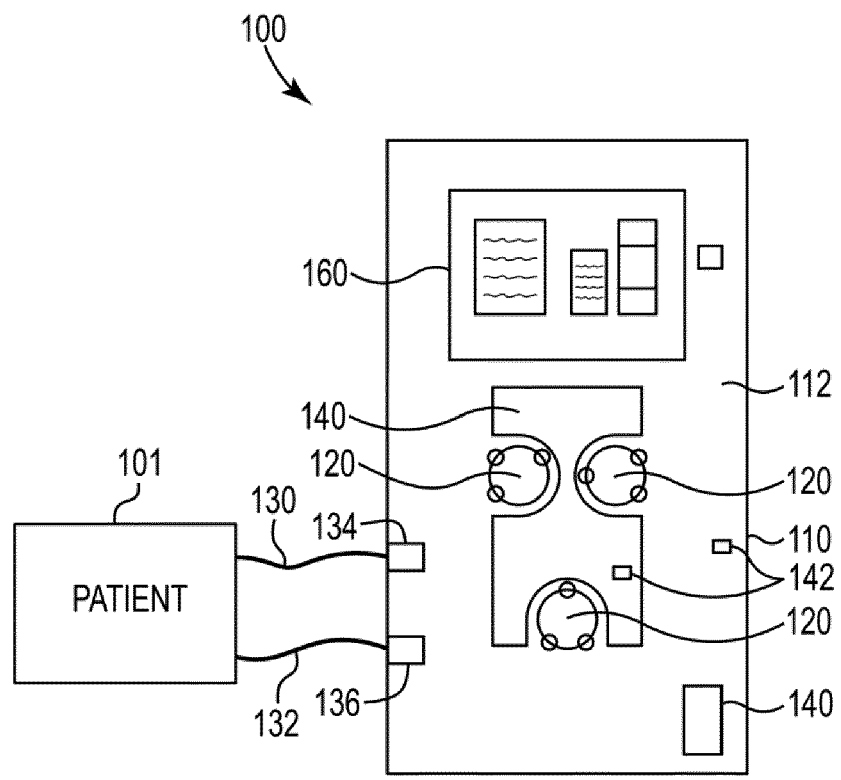
FIG. 2 is an illustration of an exemplary extracorporeal blood treatment system that may include graphical user interfaces and may utilize the methods described herein.

Referring to FIG. 2, one illustrative embodiment of an extracorporeal blood treatment system, or apparatus, 100 is depicted. The system 100 includes a housing 110 having a front face 112. The system 100 further includes one or more pumps 120, one or more disposable elements 140 (e.g., including or part of integrated modules), and one or more sensors 142 for use in performing one or more extracorporeal blood treatments. The one or more pumps 120 may be used to move liquids through the system as part of a treatment process. Although the pumps 120 are depicted in the form of peristaltic pumps, the pumps used in the extracorporeal blood treatment system described herein may be provided in a variety of alternative forms, e.g., piston pumps, pumps for use with syringes, diaphragm pumps, etc. and/or may not be visible on the outside of the housing 110. The one or more disposable elements 140 may be coupled to the system 100 for using in performing the extracorporeal blood treatment. The one or more disposable elements 140 may include one or more fluid circuits such as, e.g., dialysis or dialysate fluid circuits, blood circuits, etc. and/or one or more blood treatment units such as, e.g., filters, etc. In at least one embodiment, a disposable element 140 is a cartridge or integrated unit including a plurality of various parts or portions configured to perform the extracorporeal blood treatment. Additionally, the one or more disposable elements 140 may include containers, or vessels, containing, or holding, one or more substances for use in the performance of the extracorporeal blood treatment. For example, a disposable element 140 may include a container, or vessel, holding bicarbonate, citrate, and/or dialysate/dialysis fluid, which may be operatively coupled to the dialysis/dialysate fluid circuit. Further, the disposable elements 140 may be described as providing at least a portion of the extracorporeal blood treatment fluid circuit that may be operatively coupled to one or more pumps 120 and one or more sensors 142 of the system 100 for use in performing extracorporeal blood treatments. As shown, two disposable elements 140 appear to be coupled to the front face 112 of the housing 110 of the system 100 to, e.g., integrate with the one or more other fluid circuits, pumps 120, and sensors 142 of the system 100.

As described herein, the one or more disposable elements 140 may be described as including one or more disposable fluid circuits and one or more blood treatment units operatively coupled to the one or more disposable fluid circuits. The one or more disposable elements 140 may be further described as including a blood circuit for receiving, circulating, and returning blood from/to a patient. The blood circuit may include one or more blood lines (e.g., as part of a disposable element). Further, the one or more disposable elements 140 may be further described as including a dialysis/dialysate circuit operatively coupled, or couplable, to the blood circuit to remove waste from the blood of the patient. The dialysis/dialysate circuit may receive, circulate, and return dialysis/dialysate fluid (e.g., returning dialysis/dialysate fluid including waste). The dialysis/dialysate circuit may include one or more dialysis/dialysate lines (e.g., as part of a disposable element 140). The blood treatment units may be, for example, a plasma filter, a hemodialysis filter, a hemofiltration filter, etc. Generally, the blood treatment units may be referred to as "filters."

As described herein, the system 100 may further include one or more sensors 142. As shown, two sensors 142 are identified on the system 100. One sensor 142 is located on, or coupled to, the front surface 112 of the housing 110 and another sensor 142 is located on the, or coupled to, the disposable elements 140. Additionally, the system 100 may include sensors 142 that are not visible on the outside of the housing 110, and instead, may be internal to the system 100 (e.g., within the housing 110). Generally, the system 100 may include any one or more sensors 142 so as to be able to monitor any value (e.g., any aspect, setting, level, condition, event internal to the system 100, etc.) of any process feature of the system 100 such as, e.g., process features during the performance of one or more extracorporeal blood treatments. For example, the system 100 may include one or more pressure sensors 142 operable to measure, or monitor, various pressures of various circuits, chambers, pods, reservoirs, etc. of the system 100, e.g., during the performance of an extracorporeal blood treatment, during the performance of a pre-treatment process, during the performance of a disinfection, post-treatment process, etc. Further, for example, the system 100 may include one or more flow rate sensors 142 operable to measure, or monitor, various fluid flow rates of fluids within various circuits, chambers, pods, reservoirs, etc. of the system 100, e.g., during the performance of an extracorporeal blood treatment, during the performance of a pre-treatment process, during the performance of a disinfection, post-treatment process, etc. Specifically, the system 100 may include one or more blood-related parameter sensors 142 such as, e.g., flow rate sensors to monitor various blood flow rates throughout the blood circuits of the system 100, blood pressure sensors to monitor the diastolic and systolic blood pressure of the patient, blood circuit pressure sensors to monitor the arterial and venous blood lines pressures, heart rate sensors to measure the patient's heart rate, etc. Further, for example, the system 100 may include one or more waste sensors 142 configured to, or operable, to measure, or monitor, an amount of waste being removing from a patient (e.g., from a patient's blood), e.g., during the performance of an extracorporeal blood treatment. Further, for example the system 100 may include one or more fluid circuit or lines sensors 142 such as, e.g., blood circuit sensors to detect whether a blood circuit is coupled or uncoupled to the system, dialysate/dialysis fluid circuit sensors to detect whether a dialysate/dialysis circuit is coupled or uncoupled to the system, etc. In other words, one or more blood circuit sensors may be configured to detect whether a blood circuit is operatively coupled to the remainder of the extracorporeal blood treatment apparatus for use in an extracorporeal blood treatment and/or one or more dialysate/dialysis fluid circuit sensors may be configured to detect whether a dialysate/dialysis circuit is operatively coupled to the remainder of the extracorporeal blood treatment apparatus for use in an extracorporeal blood treatment. In one or more embodiments, the blood circuit and dialysate/dialysis fluid circuits may include some or all of the same sensors (e.g., when the blood circuit and dialysate/dialysis fluid circuit are part of the same disposable element or cartridge). Still further, for example, the system 100 may include other sensors 142 such as fluid level sensors, temperature sensors, leak detection sensors, etc. that may be used before an extracorporeal blood treatment is performed, during the performance of an extracorporeal blood treatment, and/or after an extracorporeal blood treatment is performed.

Additionally, the extracorporeal blood treatment fluid circuit of the system 100 may be described as being completed by a combination of the disposable elements 140 and the system 100 and may be generally described as defining a blood circuit that removes blood from a patient, for example, via a catheter inserted in a vascular access of the patient, and takes the blood though a blood removal line. Then, the blood may pass through a chamber (e.g., a blood chamber) and, via a return line, may be transported back to the patient.

In one or more embodiments, the extracorporeal blood treatment system 100 may be configured for acute blood treatments (e.g., continuous renal replacement therapy) and may also include one or more devices, apparatus, and structures configured to perform the acute blood treatments. For example, the extracorporeal blood treatment system 100 may include reservoir sensors, or scales, (e.g., weight sensors, load cells, etc.), each of which is configured to hold and weigh a reservoir. The reservoir sensors may be positioned below the bottom end of the housing 110, at least in part because the reservoirs are typically attached to and hang from the reservoir sensors. The extracorporeal blood treatment systems described herein may include one or more reservoir sensors and associated reservoirs such as, e.g., as few as two reservoirs sensors and associated reservoirs, four or more reservoirs sensors and associated reservoirs, etc.

The extracorporeal blood treatment system 100 further includes a venous blood line/circuit 130 extending from a patient 101 (symbolically represented in FIG. 2) to the housing 110 to return blood to the patient 101 after the blood is treated by the system 100, an arterial blood line/circuit 132 extending from the patient 101 to the housing 110 to withdraw blood from the patient 101 for treatment, a venous blood circuit pressure sensor 134 configured to measure, or monitor, the pressure of the venous blood line/circuit 130 (e.g., the pressure of the blood, or fluid, within the venous blood line/circuit 130), and an arterial blood circuit pressure sensor 136 configured to measure, or monitor, the pressure of the arterial blood line/circuit 132 (e.g., the pressure of the blood, or fluid, within the arterial blood line/circuit 132). The venous and arterial blood circuits 130, 132 may connect the patient to a blood circuit (e.g., a disposable element 140) such that, e.g., blood of the patient may be circulated through the blood circuit to perform blood treatments thereon. In other words, the blood circuit may be connectable to a patient using the venous and arterial blood lines 130, 132.

The extracorporeal blood treatment system 100 also includes a display 160 used to show, or convey, information to an operator or user. The display 160 may also serve as an input device if, e.g., the display 160 is in the form of a touchscreen (e.g., a user interactable graphical user interface, a touchscreen keyboard, etc.). Also, although the display 160 is depicted as being located in the housing 110, in one or more alternate embodiments, the display 160 may be separate from the housing 110 of the extracorporeal blood treatment system 100. For example, the display 160 may be movably (e.g., swivel, tilt, etc.) attached, or coupled, to the housing 110 (e.g., a top end of the housing 110).

As shown in FIG. 1 and as related to FIG. 2, the treatment apparatus 24 may be operatively coupled, or connected, to the computing apparatus 12. Among the treatment apparatus 24 operably coupled to the computing apparatus 12 may be the pumps 120, blood circuits/lines 130, 132, blood circuit pressure sensors 134, 136, and disposable elements 140 as shown in FIG. 2.

Exemplary graphical user interfaces, or portions thereof, for use in displaying information related to extracorporeal blood treatments, providing functionality to a user for use in preparing and performing extracorporeal blood treatments (e.g., controlling performance and/or one or more processes of a treatment), and/or configuring or maintaining an extracorporeal blood treatment system are depicted in FIGS. 5-10. Such exemplary graphical user interfaces may be depicted by the display apparatus 22 of the system 10 described herein with reference to FIG. 1 and/or the display 160 of the system 100 of FIG. 2. Additionally, the graphical user interfaces described herein may be depicted on a touchscreen, and in such configuration, the input apparatus would also be the touchscreen.

Each exemplary graphical user interface of the exemplary extracorporeal blood treatment systems and methods described herein may include one or more graphical elements, regions, and areas used to display information to a user. A user may use input apparatus 20 of the exemplary extracorporeal blood treatment system 10 described herein with reference to FIG. 1 to select or manipulate graphical elements, regions, and areas of the exemplary graphical user interfaces of FIGS. 5-10. As used herein, when a user "selects" or "interacts with" a graphical element, area, and/or region of the graphical user interface, it is to be understood that "selecting" or "interacting with" the graphical element, area, and/or region to perform one or more tasks or steps may be conducted in many different ways using many different types of input apparatus. For example, when the input apparatus includes a touch screen, a user may select or interact with a graphical element, area, and/or region by "touching" the graphical region with their finger or using a pointing device such as a stylus. Further, for example, when the input apparatus includes a mouse or similar pointing device, a user may select or interact with a graphical element, area, and/or region by locating an arrow or cursor over the desired graphical region "clicking" the graphical region. Still further, for example, when the input apparatus includes a series of buttons and/or knobs, a user or user may select or interact with a graphical element, area, and/or region by using the buttons and/or knobs to navigate to the graphical region and to select it (e.g., by depressing the button and/or knob). Additionally, it is to be understood that selection of or interaction with a graphical element, area, and/or region may be conducted using various gestures such as, for example, but not limited to, swipes, double taps, select-and-drag, press, tracing of various shapes, pinch-inwardly, pinch-outwardly, finger spread, multi-finger touches and/or swipes, etc.

As described herein, the exemplary systems and methods may provide a normal workflow. A normal workflow may be defined as a plurality of steps, or tasks, for, e.g., the preparation of an extracorporeal blood treatment, the performance of an extracorporeal blood treatment, the performance of post-treatment processes (such as, e.g., disinfection of the extracorporeal blood treatment apparatus), and the performance of processes of an extracorporeal blood treatment system that do not involve an extracorporeal blood treatment (such as, e.g., maintenance of the extracorporeal blood treatment system, set up of extracorporeal blood treatment system for a clinic, etc.). The normal workflow may be further described as being an "intended" workflow, which may be set or defined by a user (e.g., an administrator of a clinic, a system manufacturer, etc.). For example, a normal workflow may be defined, or configured, by one or more various selections or inputs by a user. For example, the normal workflow may be at least in part defined by the treatment to be performed, which may be selected by a user. For example, the normal workflow may be in part defined by a prescription for treatment. For instance, a prescription may include a specific type of anticoagulation, which may affect, or define, one or more steps of the normal workflow to account for the use of the specific type of anticoagulation. Further, for instance, a prescription may include a volume of ultrafiltration to be performed, which may affect, or define, one or more steps of the normal workflow to perform the prescribed amount of ultrafiltration. Further, for instance, a prescription may include sodium settings, bicarbonate settings, anticoagulation settings, time, treatment modality, and ultrafiltration volume, which may affect, or define, one or more steps of the normal workflow.

To indicate to a user the next step of the plurality of steps of a normal workflow, an exemplary graphical user interface may display one more workflow affordances to indicate to users which of and how a plurality of process feature graphical elements displayed on the graphical user interface may be used to perform the plurality of steps of the normal workflow as will be described herein with reference to FIG. 3.

Figure 3:
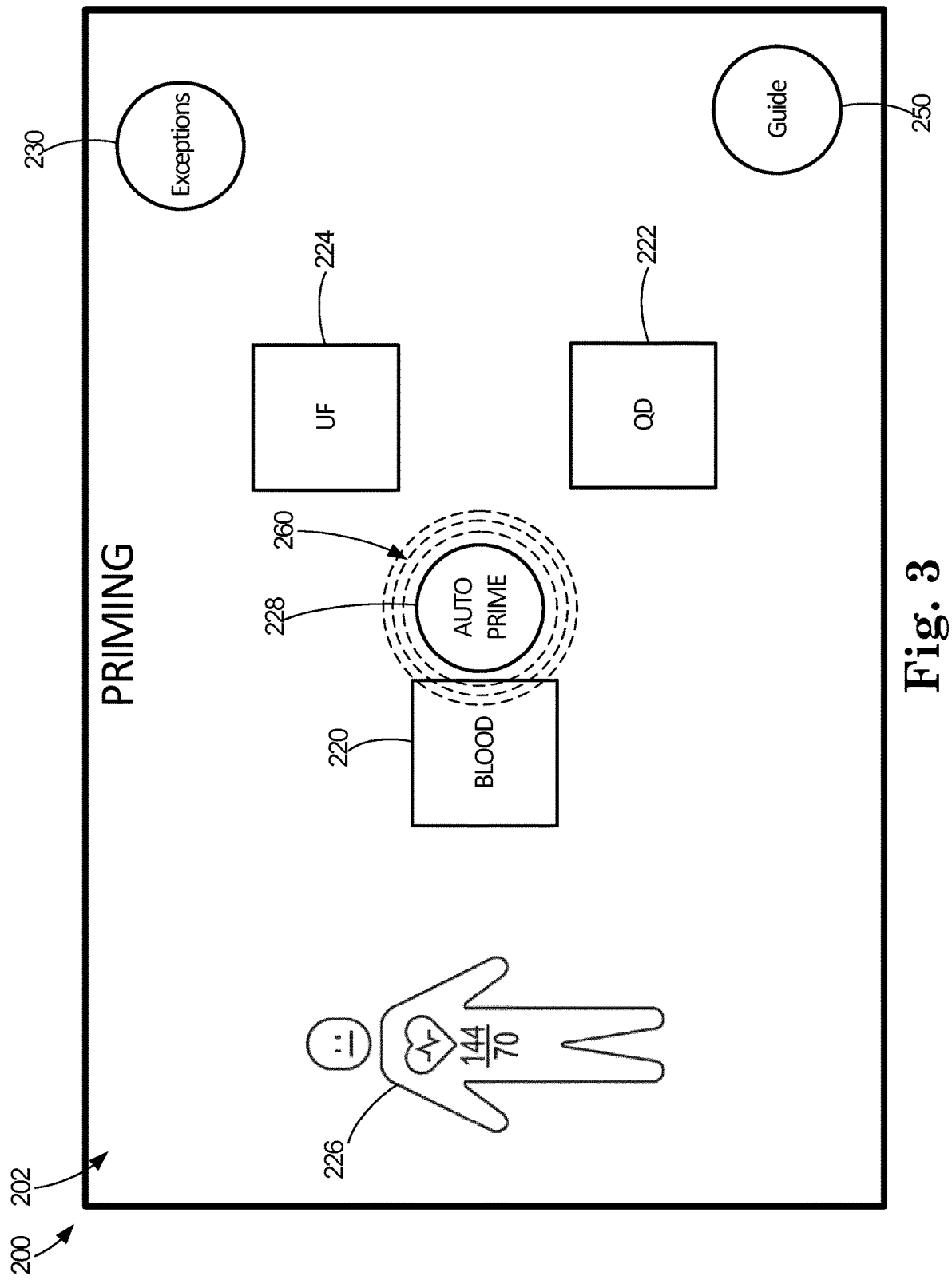
FIG. 3 depicts an exemplary graphical user interface displaying a plurality of process feature graphical elements for use with extracorporeal blood treatment systems such as, for example, shown generally in FIGS. 1-2.

For example, an exemplary graphical user interface 200 including an operation region 202 is depicted in FIG. 3. Within the operation region 202 of the graphical user interface 200, the graphical user interface 200 may display a plurality of process feature graphical elements used to perform various processes and display various information with respect to the treatment. More specifically, the operation region 202 may include a blood process feature graphical element 220 configured to perform various processes and display information related to the patient's blood, a dialysate ("QD") process feature graphical element 222 configured to perform various processes and display information related to dialysate, and an ultrafiltration process feature graphical element 224 ("UF") configured to perform various processes and display information related to ultrafiltration.

Further, the operation region 202 may include an action process feature graphical element 228 configured to perform various actions related to a plurality of processes and a patient process feature graphical element 226 (e.g., the patient process feature graphical element 226 may be human-shaped or define the shape of a human) configured to perform various processes and display information related to the patient. The action process feature graphical element 228 may be configured to be spatially related to the blood process feature graphical element 220, the dialysate process feature graphical element 222, and the ultrafiltration process feature graphical element 224 such that the position, or location, of the process feature graphical elements 220, 222, 224 with respect to the action process feature graphical element 228 may be indicative of the states of the process features represented by and associated with the process feature graphical elements 220, 222, 224. In other words, the action process feature graphical element 228 may be described as a central operating point or area from which the process feature graphical elements 220, 222, 224 may be located about, and the distance the process feature graphical elements 220, 222, 224 are located away from the action process feature graphical element 228 (e.g., the central operating point) may indicate to a user (e.g., at a glance or quick look) the status of the process features represented by and associated with such process feature graphical elements 220, 222, 224. The patient process feature graphical element 226 may be selected to perform a pulse measurement or blood pressure measurement or may be moved (e.g., selected and dragged) to indicate whether a patient is connected or disconnected from a blood/dialysate circuit of the blood treatment system. Further, as shown, the patient process feature graphical element 226 may further display the patient's systolic and diastolic blood pressure.

Still further, the operation region 202 may include, or depict, one or more affordances, or affordance indications, to indicate to users which and how the process feature graphical elements are to be interacted with for various reasons such as, e.g., to indicate the next step of a normal workflow. The affordances may include any one or more graphics that indicate to users which and how the process feature graphical elements are to be interacted with. For example, some affordances may be configured to indicate to a user that a particular process feature graphical element is to be selected (e.g., clicked, touched, etc.) and moved (e.g., dragged, etc.) in a particular direction. Further, for example, some affordances may be configured to indicate to a user that a particular process feature graphical element is to be only selected (e.g., clicked, touched, etc.). Still, for example, some affordances may be configured to indicate to a user that one or more tasks should be completed with respect to the treatment systems and/or patient (e.g., connect a patient to the blood lines, install and/or remove a filter cartridge, install and/or remove anticoagulation apparatus, etc.). The affordances may include blinking graphics, moving "shadows," or semi-transparent representations, of process feature graphical elements, lines, semi-transparent lines, various coloration, animations, text (e.g., "Press Here," "Select Here," text timers or "countdowns," etc.) and/or arrows. In one or more embodiments, the affordances may not be continuously displayed on the graphical user interface 200, and instead, may disappear, or be removed from the graphical user interface 200, in response to expiration of a selected time period. In other words, the affordances may have an expiration time upon which the affordances may cease to be displayed as opposed to a continuous affordance which would only cease to be displayed in response to an event such as a user performing the intended task. Further, such affordances that are not continuous may include a textual display of the amount of time left before the affordances expire. In other words, a timer or countdown may be displayed proximate or as part of such affordances to indicate to users how much time is left before the affordances expire or disappear.

In one or more embodiments, the affordances described herein may not be displayed on the graphical user interface 200, and instead, be presented to users using auditory and haptic feedback. For example, the affordances may include sounds (e.g., voice commands, etc.) output by various sound output apparatus. Further, for example, the affordances may include a vibrational or haptic response on a watch or other personal computing item that may be worn or carried by a user.

As noted herein, workflow affordances may be displayed on the graphical user interface 200 to indicate to users which of and how a plurality of graphical elements displayed on the graphical user interface may be used to perform the plurality of steps of the normal workflow. As shown, in FIG. 3, the exemplary graphical user interface 200 may be described as depicting a portion of a "priming" process of a treatment preparation portion of a normal workflow. The blood process graphical feature element 220 has been moved proximate (e.g., in contact with) the action process feature graphical element 228 to indicate that the blood circuit of the extracorporeal blood treatment apparatus has been operatively coupled, or connected, to the remainder of the extracorporeal blood treatment system.

The next step, or task, in the normal workflow for the priming process is indicated by the workflow affordance 260, which is a graphical animation proximate the action process feature graphical element 228, to indicate to user to select, or touch, the action process feature graphical element 228 to initiate, or start, the priming process of the treatment preparation portion of the normal workflow. Although the workflow affordance 260 is statically depicted in FIG. 3 as three concentric, dashed-line circles surrounding the action process feature graphical element 228, it is to be understood that such concentric, dashed-line circles are representative of a graphical animation of the workflow affordance 260 to indicate to user to select, or touch, the action process feature graphical element 228 to trigger the priming process. For example, the graphical animation of the workflow affordance 260 could include various blinking, or flashing, colors and/or shapes surrounding or proximate the action process feature graphical element 228. Further, for example, the graphical animation of the workflow affordance 260 could include a moving "shadow," or semi-transparent representation, of the action process feature graphical element 228. Still further, for example, the graphic animation of the workflow affordance 260 could include a periodic shrinking and/or growing of the action process feature graphical element 228 (e.g., the size of the action process feature graphical element 228 could increase and then decrease periodically, the action process feature graphical element 228 could pulsate, etc.).

Figure 4A:
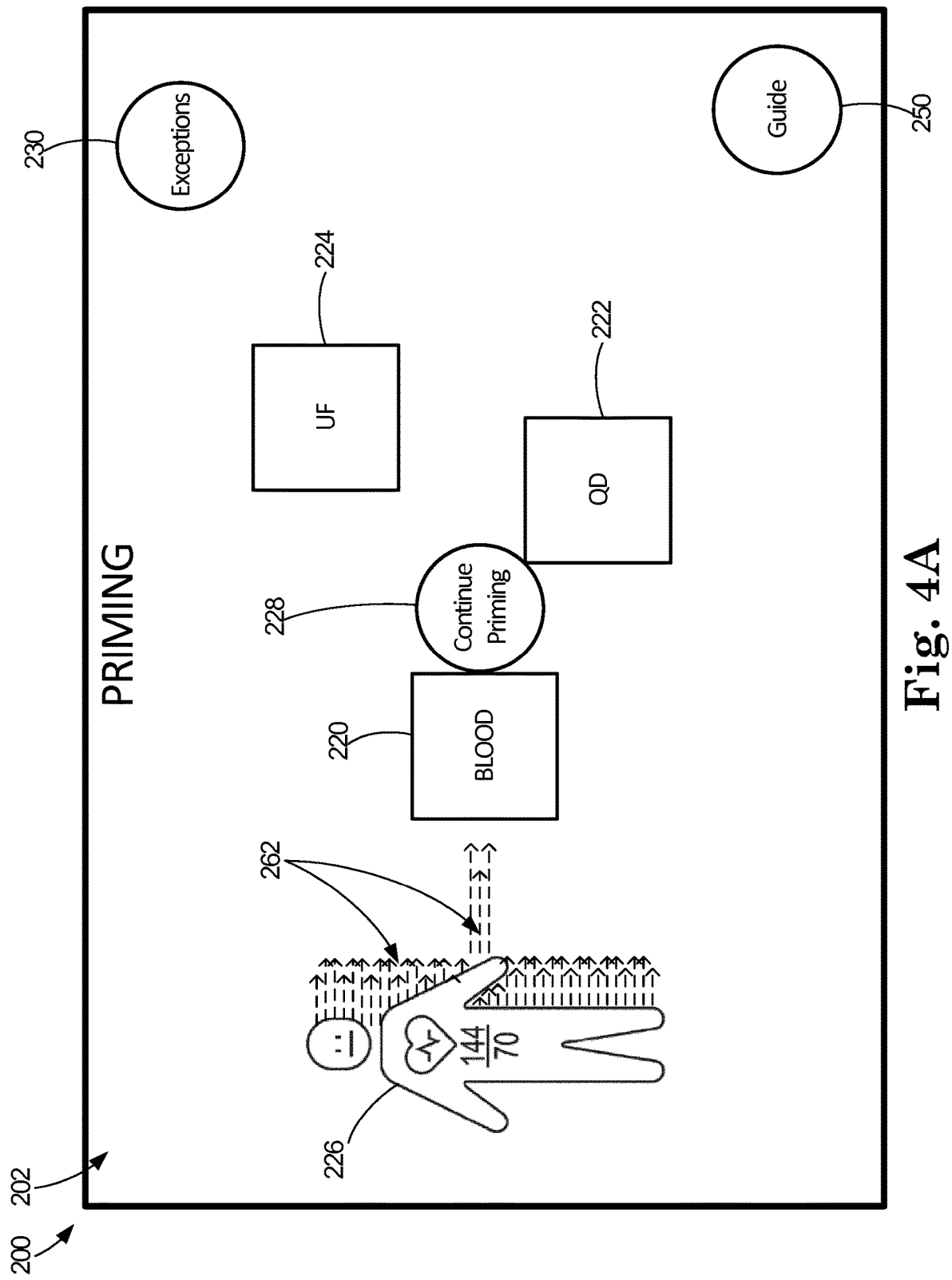
FIG. 4A depicts the graphical user interface of FIG. 3 displaying workflow affordances with respect to a blood process feature graphical element and an action process feature graphical element for use in the preparation of an extracorporeal blood treatment.

As shown in FIG. 4A, a user has selected the action process feature graphical element 228, which has initiated the priming process of the extracorporeal blood treatment system. A shown, the workflow affordance 260 has been removed from the graphical user interface 200 (e.g., not displayed any longer, disappeared, etc.) in response to selection of the action process feature graphical element 228. Further, selection of the action process feature graphical element 228 has moved the dialysate process feature graphical element 222 to be proximate, or in contact with, the action process feature graphical element 228 to indicate that the dialysate circuit is operatively coupled to the blood circuit. The next step in the normal workflow may include connecting the patient to the extracorporeal blood treatment system and beginning the blood treatment.

To indicate the next step in, or of, the normal workflow, the exemplary graphical user interface 200 may depict one or more workflow affordances such as shown in FIG. 4A. More specifically, a workflow affordance 262 has been depicted proximate the patient process feature graphical element 226 to indicate to user that selection and movement of the patient process feature graphical element 226 towards the blood process feature graphical element 220 may instruct the extracorporeal blood treatment system that the patient has been connected to the blood circuit and/or dialysate circuit via one or more bloodlines. In one or more embodiments, the patient process feature graphical element 226 may be automatically moved proximate the blood process feature graphical element 220 upon the extracorporeal blood treatment system sensing that the patient has been operatively coupled to the blood circuit. The workflow affordance 262 proximate the patient process feature graphical element 226 may include oscillating movement of the patient process feature graphical element 226 towards and away from the blood process feature graphical element 220 and/or a moving "shadow," or semi-transparent representation, of the patient process feature graphical element 226. In one or more embodiments, affordances such as a workflow affordance 262 may be referred to as a patient-related affordance since, for example, it is primarily concerned with the patient. Another example of a patient-related affordance may be workflow affordance (e.g., a graphic, etc.) that indicates which access of a patient (e.g., in the situation where a patient has more than a single access) should be used for a treatment. Other affordances, which may not be primarily concerned with the patient, may be primarily concerned with the treatment systems or treatment apparatus, and thus, may be referred to as machine-related affordances.

Figure 4B:
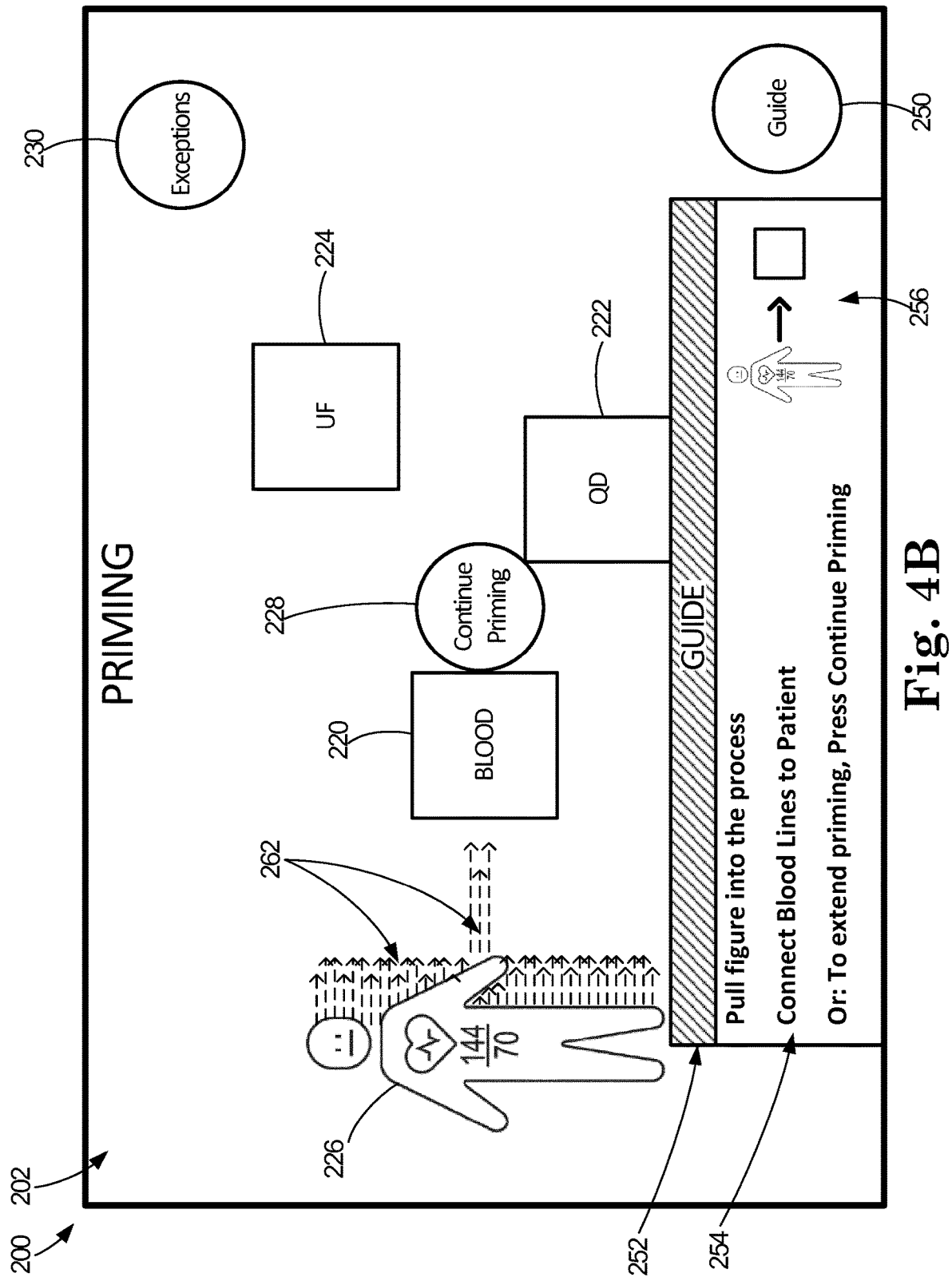
FIG. 4B depicts the graphical user interface of FIG. 4A also including a guide area.

If a user desires more information regarding the next one or more steps of the normal workflow, a user may select a guide graphical element 250 as shown depicted in the lower right corner of the operation region 202 of the graphical user interface 200. Upon selection of the guide graphical element 250, a guide graphical area 252 may be depicted as shown in FIG. 4B. The guide graphical area 252 may include information related to the next one or more steps of the normal workflow. More specifically the guide graphical area 252 may include textual and/or graphical information related to the next one or more steps of the normal workflow.

For example, as shown in FIG. 4B, the guide graphical area 252 includes textual information 254 that recites "Pull figure into the process; Connect Blood Lines to Patient; Or: To extend priming, Press Continue Priming." Further, the guide graphical area 252 includes graphical information 256 that includes a graphical depiction of the patient process feature graphical element 226 being moved proximate the blood process feature graphical element 220, which may correspond to the next step of the normal workflow and the workflow affordance 262. If user would like to remove the guide graphical area 252 from the operation region 202 of the graphical user interface 200, a user may select an area outside of the guide graphical area 252 and the guide graphical area 252 may disappear, or be removed, from the operation region 202 of the graphical user interface 200 so as to, e.g., return the graphical user interface 200 to the state shown in FIG. 5A.

Figure 5:
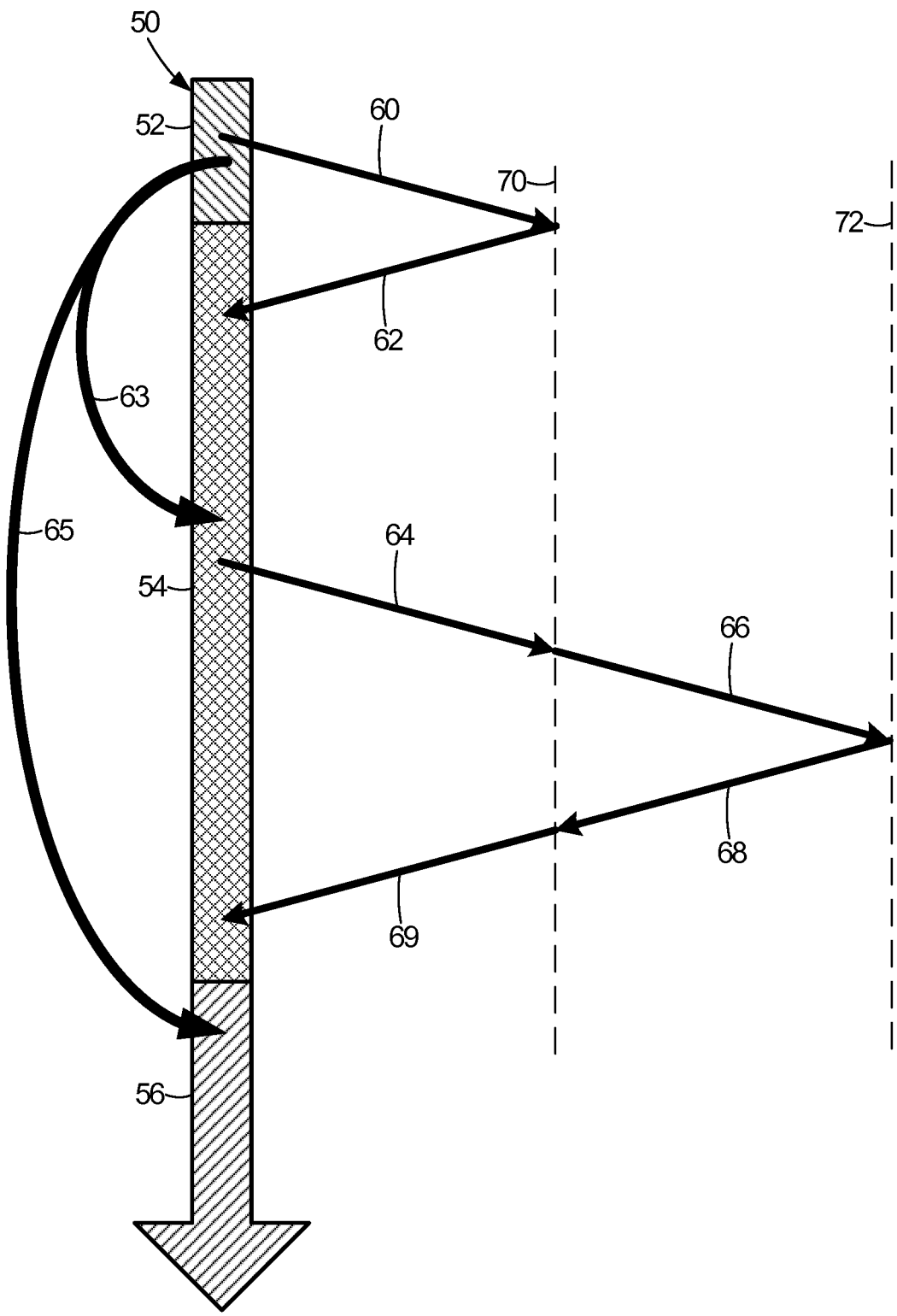
FIG. 5 is a diagram of an exemplary normal workflow including deviations and exceptions therefrom for use with an exemplary graphical user interface as, for example, shown generally in FIGS. 3-4.

In essence, the exemplary graphical user interface 200 of FIGS. 3-4 may include a plurality of workflow affordances to indicate to users which and how the plurality of process feature graphical elements are to be used to perform a plurality of steps of the normal workflow. Thus, user may be guided along the normal workflow on the graphical user interface 200 by the workflow affordances. A diagram of an exemplary normal workflow 50 is shown in FIG. 5. The normal workflow 50 is represent by an arrow extending from the top portion of the page to towards the bottom of the page and may include three portions chronologically arranged from the top to the bottom: namely, a treatment preparation portion 52, a treatment performance portion 54, and a post-treatment portion 56. Each of the treatment preparation portion 52, treatment performance portion 54, and post-treatment portion 56 may include one or more steps for performing the normal workflow 50.

A user may progress through each of the steps of the treatment preparation portion 52 and may move on to each of the steps of to the treatment performance portion 54. After the treatment portion 54 is completed, the user may move on to progressing through each of the steps of the post-treatment portion 56. Workflow affordances may be provided on the graphical user interface 200 to guide the user along each of the portions 52, 54, 56 of the normal workflow 50.

However, a user may choose to deviate from the normal workflow 50. For example, a user may deviate away from the normal workflow 50 as represented by arrow 60, and thus, be one deviation away from the normal workflow as indicated by the dotted line 70. The user may then return to the normal workflow 50 as represented by the arrow 62 and may continue the remainder of the normal workflow 50.

Figure 6:
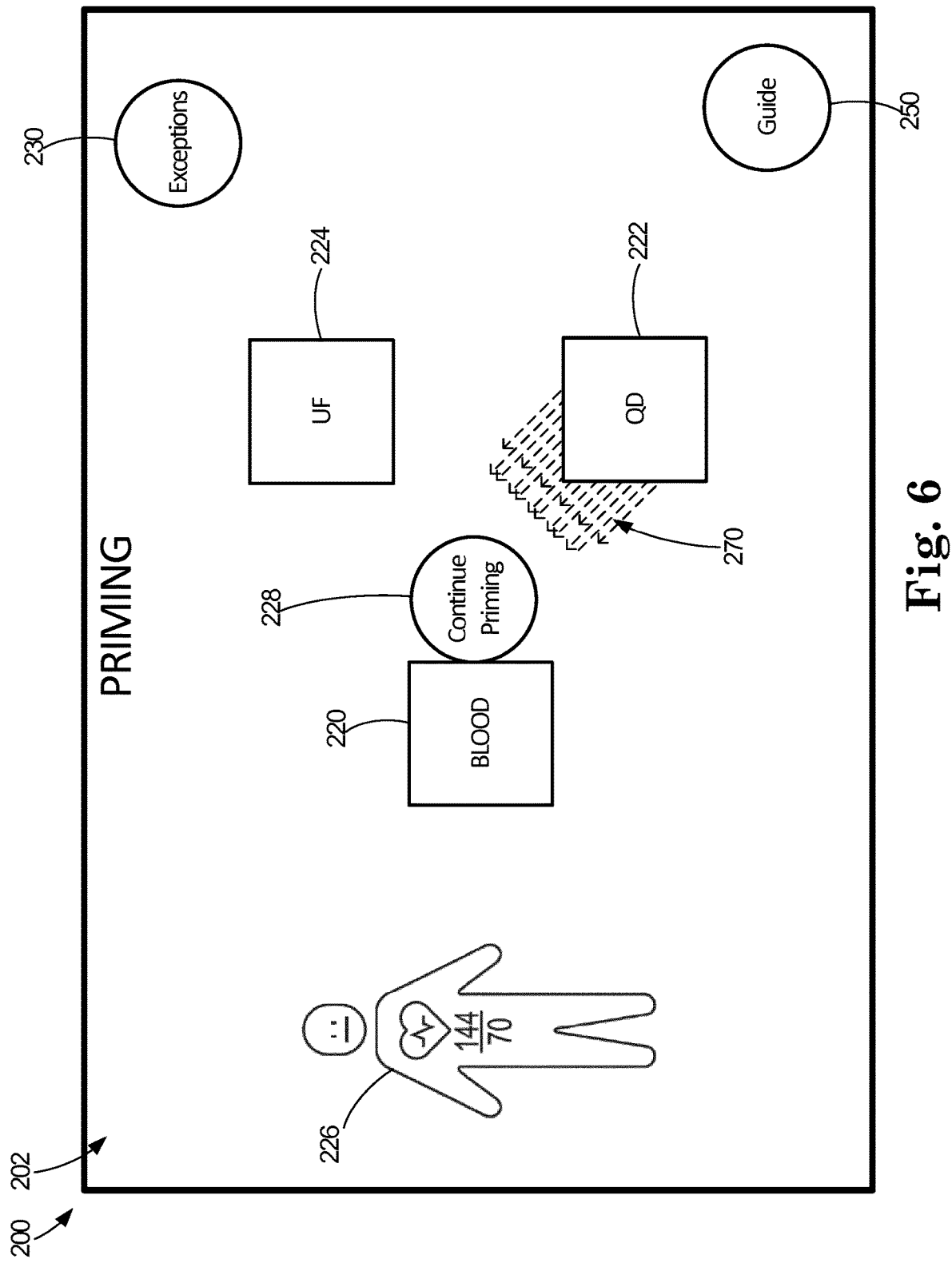
FIG. 6 depicts the graphical user interface of FIG. 4 displaying a workflow deviation affordance with respect to a dialysate process feature graphical element for use in the preparation of an extracorporeal blood treatment.

For example, during a priming portion of treatment preparation of a normal workflow, a user may select and move (e.g., drag) the dialysate process feature graphical element 222 away from the action element 228 to operatively decouple, or disconnect, the dialysate circuit from the blood circuit of the extracorporeal blood treatment apparatus as shown in the exemplary graphical user interface 200 of FIG. 6. Such disconnection of the dialysate circuit from the blood circuit of extracorporeal blood treatment apparatus may be considered a deviation from the priming portion of the normal workflow. Thus, as shown in FIG. 6, the exemplary graphical user interface 200 may depict a workflow deviation affordance 270 to indicate which of and how the plurality process feature graphical elements are to be used to return to the normal workflow. In this example, the workflow deviation affordance 270 has been depicted proximate the dialysate process feature graphical element 222 to indicate to users that selection and movement of the dialysate process feature graphical element 222 to be proximate the action process feature graphical element 228 will reconnect the dialysate circuit to the blood circuit (e.g., operatively couple the dialysate circuit to the blood circuit) thereby returning the user and system to the normal workflow. In other words, the workflow deviation affordance 270 was configured to indicate to users how to return to the normal workflow before the dialysate process feature graphical element 222 was moved away from the action process feature graphical element 228. The workflow deviation affordance 270 proximate the dialysate process feature graphical element 222 may include a moving "shadow," or semi-transparent representation, of the dialysate process feature graphical element 222 to towards and away from the action element 228.

Workflow deviation affordances such as the workflow deviation affordance 270 may be shown without workflow affordances depicted in the graphical user interface 200 as shown in FIG. 6. In this way, the workflow deviation affordances may guide a user back to the normal workflow without the user being distracted by workflow affordances or other affordances. In other words, workflow affordances may be removed from, or may not be displayed on, the graphical user interface 200 when one or more workflow deviation affordances are depicted as shown in FIG. 6.

In other embodiments, workflow affordances such as the workflow affordances 260, 262 may be shown at the same time as workflow deviation affordances such as workflow deviation affordance 270 (not depicted). Further, in this example, one or more of the actions indicated, or suggested, by the workflow affordances may automatically perform the action indicated, or suggested, by the workflow deviation affordance. For example, selection of the action process feature graphical element 228 to "Continue Priming" may automatically move the dialysate process feature graphical element 222 to be proximate, or in contact, with the action process feature graphical element 228 such that the dialysate circuit is operatively coupled to the blood circuit so as to continue priming the extracorporeal blood treatment apparatus.

A user may deviate more than one deviation away from the normal workflow 50 as further shown in FIG. 5. As shown, during the treatment portion 54, a user may deviate once as shown by line 64, and then a second time as shown by line 66. Thus, the system may be two deviations away from the normal workflow 50 as indicated by the dotted line 72. The user may then return to the normal workflow 50 as represented by each of arrows 68, 69 the arrow 62 and may continue the remainder of the normal workflow 50. Although the examples described with reference to FIG. 5 include a single deviation and two deviations, it is to be understood that the exemplary systems and methods described herein may be configured to handle more than two deviations from the normal workflow using, e.g., workflow deviation affordances. Two deviations are described herein with respect to FIGS. 7-9.

Figure 7:
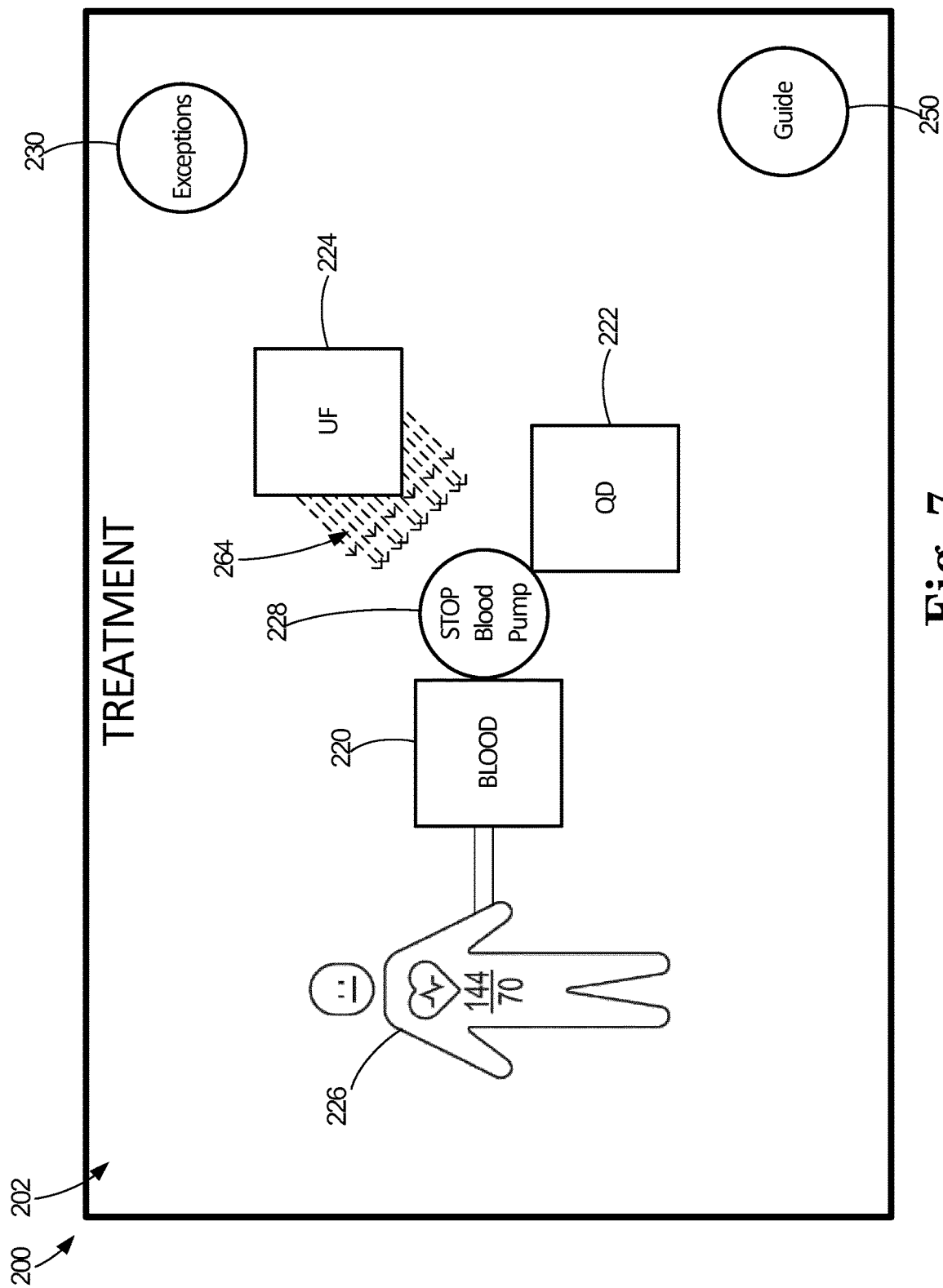
FIG. 7 depicts the graphical user interface of FIG. 3 displaying a workflow affordance with respect to an ultrafiltration process feature graphical element for use in the performance of an extracorporeal blood treatment.

A user has initiated a blood treatment as shown in the exemplary graphical user interface 200 depicted in FIG. 7. More specifically, as shown, the patient process feature graphical element 226 has been moved proximate the blood process feature graphical element 220 to indicate that the patient is connected to the extracorporeal blood treatment apparatus and the action process feature graphical element 228 has been selected to start the blood pump to perform the blood treatment.

The ultrafiltration process feature graphical element 224 may be moved proximate, or in contact with, the action process feature graphical element 228 to initiate, or trigger, one or more ultrafiltration processes. In this specific example, the ultrafiltration process feature graphical element 224 has not been moved proximate the action process feature graphical element 228. The next step of the normal workflow may be to start, or initiate, one or more ultrafiltration processes, and thus, a workflow affordance 264 is depicted proximate the ultrafiltration process feature graphical element 224 to indicate to a user that the next step in the normal workflow is to move the ultrafiltration process feature graphical element 224 proximate the action process feature graphical element 228.

Figure 8:
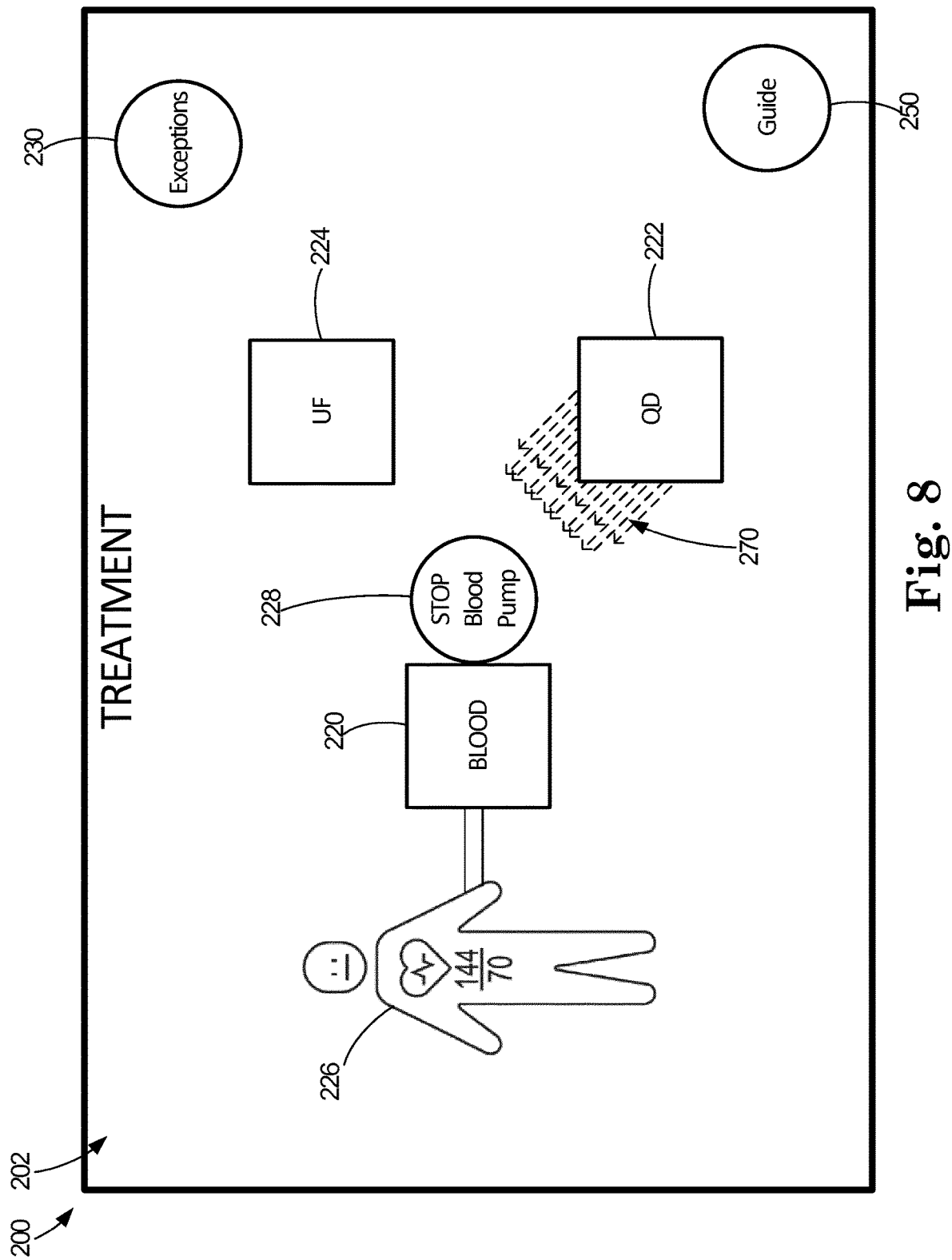
FIG. 8 depicts the graphical user interface of FIG. 7 displaying a workflow deviation affordance with respect to a dialysate process feature graphical element for use in the performance of an extracorporeal blood treatment.

During a treatment portion of a normal workflow as shown in FIG. 7, a user may select and move (e.g., drag) the dialysate process feature graphical element 222 away from the action element 228 to operatively decouple, or disconnect, the dialysate circuit from the blood circuit of the extracorporeal blood treatment apparatus as shown in the exemplary graphical user interface 200 of FIG. 8. Such disconnection of the dialysate circuit from the blood circuit of extracorporeal blood treatment apparatus may be considered a deviation from the treatment portion of the normal workflow. Thus, as shown in FIG. 8, the exemplary graphical user interface 200 may depict a workflow deviation affordance 270 to indicate which of and how the plurality process feature graphical elements are to be used to return to the normal workflow. In this example, the workflow deviation affordance 270 has been depicted proximate the dialysate process feature graphical element 222 to indicate to users that selection and movement of the dialysate process feature graphical element 222 to be proximate the action process feature graphical element 228 will reconnect the dialysate circuit to the blood circuit (e.g., operatively couple the dialysate circuit to the blood circuit) thereby returning the user and system to the normal workflow.

Figure 9:
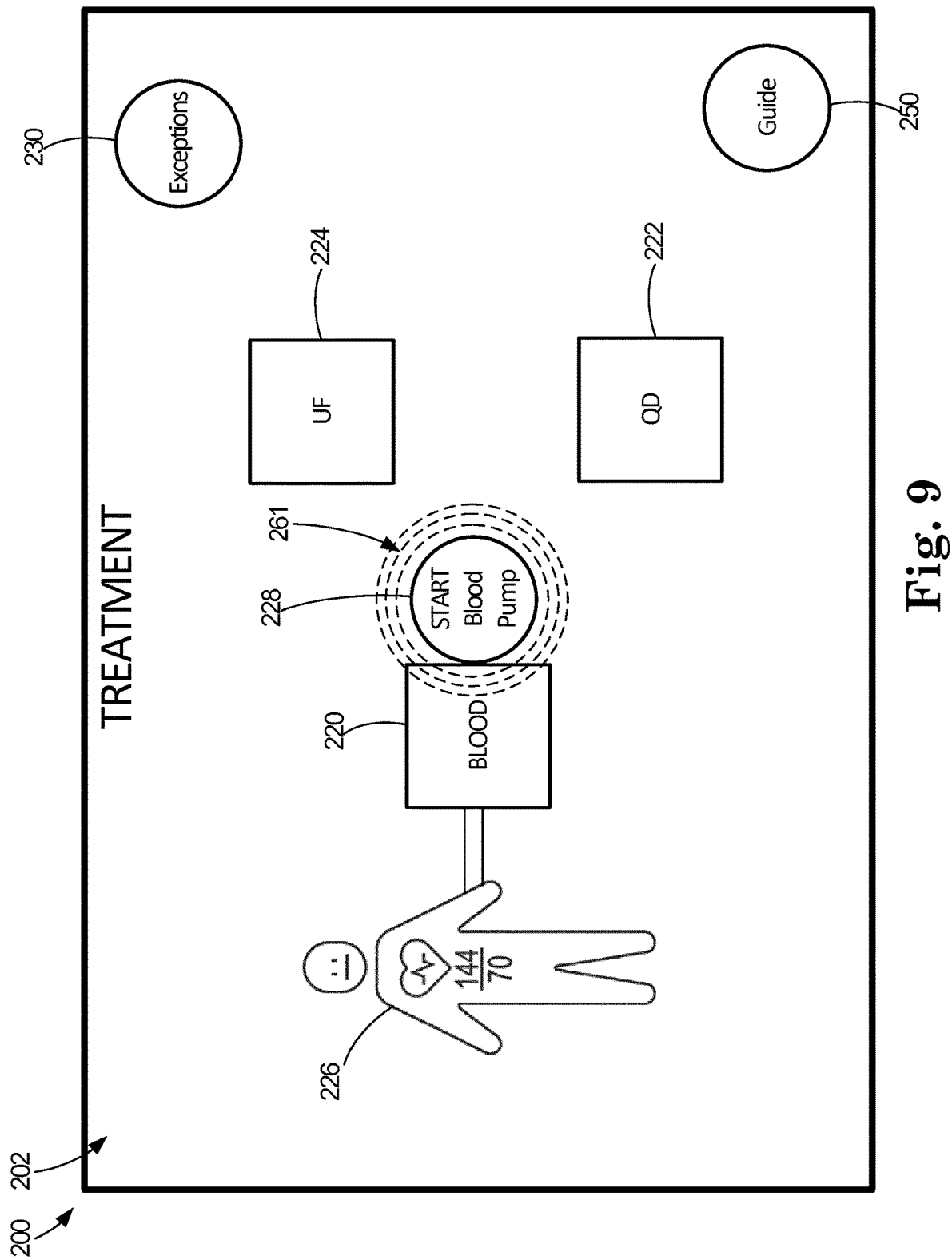
FIG. 9 depicts the graphical user interface of FIG. 8 displaying an additional workflow deviation affordance with respect to an action process feature graphical element for use in the performance of an extracorporeal blood treatment.

While being one deviation from the normal workflow as shown in FIG. 8, a user may further deviate as shown in FIG. 9. For example, a user may select (e.g., touch) the action process feature graphical element 228 to operatively stop the blood pump of the extracorporeal blood treatment apparatus as shown in the exemplary graphical user interface 200 of FIG. 9. The stoppage, or halting, of the blood pump may be considered a further deviation from the treatment portion of the normal workflow than when the dialysate process feature graphical element 222 was moved away from the action process feature graphical 228 in FIG. 8. Thus, as shown in FIG. 9, the exemplary graphical user interface 200 may depict a workflow deviation affordance 261 to indicate which of and how the plurality process feature graphical elements are to be used to return to the normal workflow. In this example, the workflow deviation affordance 261 has been depicted proximate the action process feature graphical element 228 to indicate to users that selection of the action process feature graphical element 228 will re-start the blood pump thereby returning the user and system to one deviation, or step, closer to the normal workflow. For example, upon selection of the action process feature graphical element 228 in FIG. 9 to re-start the blood pump, the graphical user interface 200 of FIG. 8 would be displayed, which includes displaying the workflow deviation affordance 270 to select and move the dialysate process feature graphical element 222 back, or in proximate to, the action process feature graphical element 228. Thus, the workflow deviation affordance 261 may indicate to a user how to return to being one deviation away from the normal workflow, which is shown in FIG. 8, and the workflow deviation affordance 270 may indicate to a user how to return the normal workflow as shown in FIG. 7. Further, as shown in this example, only one workflow deviation affordance is shown, or displayed, at a time. In other embodiments, more than one workflow deviation affordance may be shown, or displayed, at the same time.

Additionally, a user may desire, or intend, to skip one or more steps of the normal workflow 50 to perform another portion of the normal workflow 50 or terminate the performance of the normal workflow 50. For example, a user may want to skip, or jump, from the middle of a treatment portion 54 of the normal workflow 50 to post-treatment 56 (e.g., including disinfection) of the normal workflow 50. Further, for example, as user may want to skip from just prior to a post-treatment portion 56 (e.g., including disinfection) of the normal workflow 50 to the treatment preparation portion 52 so as to perform another treatment prior to disinfecting or performing other post-treatment steps of a normal workflow. Still further, for example, a user may want to skip to a disinfection processes or other processes of a post-treatment portion 56 of the normal workflow 50 from the treatment preparation portion 52.

The "skipping" or "jumping" from one step of the normal workflow or from one portion of the normal workflow to another may be referred to as an "exception" to the normal workflow 50. As shown in the diagram of FIG. 5, an exception skipping from the treatment preparation portion 52 to the post-treatment process portion 56 is represented by arrow 65, and another exception skipping from the treatment preparation portion 52 to the treatment process portion 54 is represented by arrow 63. The exemplary systems and methods described herein may be configured to provide, or generate, exceptions to the normal workflow 50 using one or more process feature graphical elements as further described with respect to FIGS. 7-10.

Figure 10:
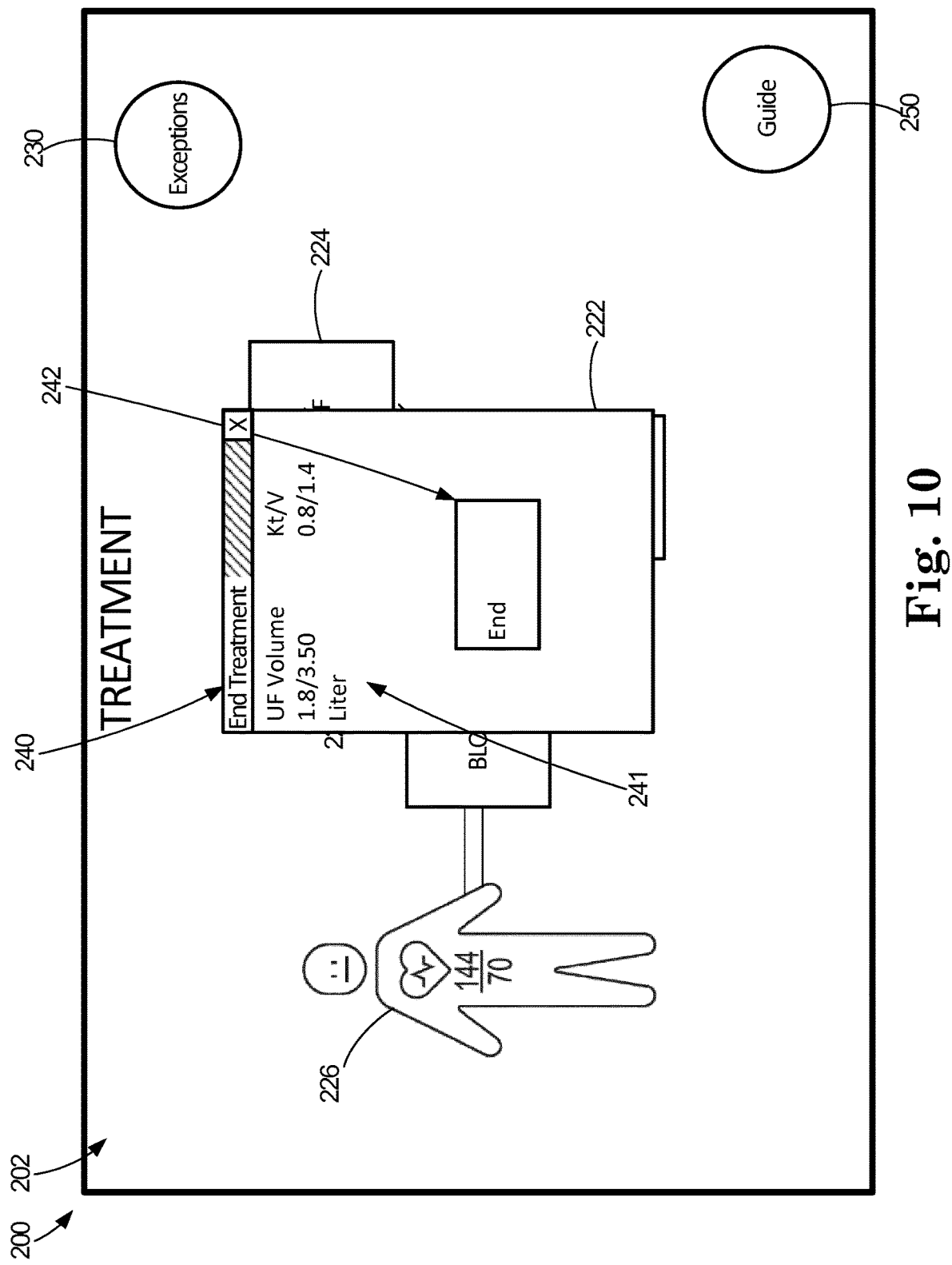
FIG. 10 depicts the graphical user interface of FIGS. 7-9 displaying an exceptions graphical area.

For example, a user may decide to end the blood treatment thereby deviating from the normal workflow in the form of an exception. To do so, a user may select an exceptions graphical element 230 as shown depicted in the upper right corner of the operation region 202 of the graphical user interface 200 of FIGS. 7-9. Upon selection of the exceptions graphical element 230, an exceptions graphical area 240 may be depicted on the exemplary graphical user interface 200 as shown in FIG. 10. The exceptions graphical area 240 may include information 241 related to the one or more processes being presently preformed and one or more deviation graphical elements 242, which upon selection may trigger, or initiate, the exception. In this example, the information 241 of the exceptions graphical area 240 includes information related to the performance of the blood treatment such as, e.g., UF Volume and Kt/V. A user may select (e.g., touch, click, etc.) the deviation graphical element 242 to "end" the blood treatment skipping the remainder of the one or more steps of the treatment portion of the normal workflow to another portion of the normal workflow such as post-treatment processes including disinfection.

Although a single deviation graphical element is depicted in the exceptions graphical area 240, it is to be understood that some portions or steps of the normal workflow may include more than one deviation graphical element to, for example, provide more than one option when deviating from the normal workflow.

Other example of exceptions may include initiating post-treatment processes such as disinfection from treatment preparation or during an ongoing treatment, beginning a new treatment without performing all or most of the post-treatment processes such as disinfection, etc.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the systems and methods described herein. Various modifications of the illustrative embodiments, as well as additional embodiments of the disclosure, will be apparent upon reference to this description.

What is claimed is:

1. A medical treatment system comprising:
   treatment apparatus comprising one or more pumps and one or more sensors;
   a display comprising a graphical user interface, wherein the graphical user interface is configured to display a plurality of process feature graphical elements related to preparing a treatment, performing a treatment, and performing post-treatment processes, wherein each process feature graphical element of the plurality of process feature graphical elements corresponds to a different process feature of the medical treatment system; and
   a computing apparatus comprising one or more processors, wherein the computing apparatus is operatively coupled to the treatment apparatus and the display, wherein the computing apparatus is configured to:
      display a plurality of process feature graphical elements on the graphical user interface to be used by a user to prepare a treatment, to perform a treatment, and to perform post-treatment processes, wherein the plurality of process feature graphical elements comprises at least one of a blood process feature graphical element corresponding to a blood circuit of the treatment apparatus, a dialysate process feature graphical element corresponding to a dialysate circuit of the treatment apparatus, an ultrafiltration process feature graphical element corresponding to one or more ultrafiltration processes, and a patient process feature graphical element representative of the patient and connection of the patient to a blood circuit of the treatment apparatus,
      define a normal workflow comprising a plurality of steps for the preparation of a treatment, the performance of the treatment, and the performance of post-treatment processes,
      display one or more of a plurality of workflow affordances on the graphical user interface to indicate to a user which of and how the plurality of process feature graphical elements are to be used to perform the plurality of steps of the normal workflow, and
      display a workflow deviation affordance on the graphical user interface in response to a user deviating from the normal workflow, wherein the workflow deviation affordance indicates which of and how the plurality of process feature graphical elements are to be used to return to the normal workflow.

2. The system of claim 1, wherein the computing apparatus is further configured to remove the one or more of the plurality of workflow affordances from the graphical user interface in response to display of the workflow deviation affordance.

3. The system of claim 1, wherein displaying a workflow deviation affordance on the graphical user interface in response to a user deviating from the normal workflow comprising displaying a workflow deviation affordance on the graphical user interface in response to the user deviating from the normal workflow using the plurality of process feature graphical elements.

4. The system of claim 1, wherein the normal workflow is at least partially defined by a prescription.

5. The system of claim 4, wherein the prescription comprises one or more of sodium settings, bicarbonate settings, anticoagulation settings, time, treatment modality, and ultrafiltration volume.

6. The system of claim 1, wherein the computing apparatus is further configured to display, after the display of workflow deviation affordance on the graphical user interface, an additional workflow deviation affordance on the graphical user interface in response to a user deviating further from the normal workflow using the plurality of process feature graphical elements, wherein the additional workflow deviation affordance indicates which of and how the plurality of process feature graphical elements are to be used to return to being on deviation away from the normal workflow.

7. The system of claim 6, wherein the computing apparatus is further configured to remove the workflow deviation affordance from the graphical user interface in response to display of the additional workflow deviation affordance.

8. The system of claim 1, wherein the computing apparatus is further configured to:
   display an exceptions graphical element to allow a user to deviate from the normal workflow, and
   display one or more deviations graphical elements in response to selection of the exceptions graphical element, wherein the one or more deviations graphical elements are selectable to initiate a deviation from the normal workflow.

9. The system of claim 8, wherein the one or more deviation graphical elements to deviate from the normal workflow comprise an end treatment graphical element to end an ongoing treatment when the treatment is being performed.

10. The system of claim 8, wherein the one or more deviation graphical elements to deviate from the normal workflow comprise an initiate disinfection graphical element to initiate disinfection of the treatment apparatus when a treatment is being prepared.

11. The system of claim 8, wherein the one or more deviation graphical elements to deviate from the normal workflow comprise a new treatment graphical element to initiate the preparation of a treatment without disinfecting the treatment apparatus when post-treatment processes are being performed.

12. The system of claim 1, wherein the computing apparatus is further configured to:
   display a guide graphical element, and
   display a guide area comprising information related to the next step of the plurality of steps of the normal workflow to be performed to continue the normal workflow in response to selection of the guide graphical element.

13. The system of claim 1, wherein the plurality of process feature graphical elements comprises:
   the blood process feature graphical element corresponding to a blood circuit of the treatment apparatus;

the dialysate process feature graphical element corresponding to a dialysate circuit of the treatment apparatus; and the ultrafiltration process feature graphical element corresponding to one or more ultrafiltration processes.

14. The system of claim 1, wherein the plurality of process feature graphical elements comprises the patient process feature graphical element representative of the patient and connection of the patient to a blood circuit of the treatment apparatus.

15. The system of claim 1, wherein the plurality of workflow affordances and the deviation workflow affordance comprises a graphical animation to indicate a direction that a process feature graphical element is to be moved.

16. The system of claim 1, wherein the plurality of workflow affordances and the deviation workflow affordance comprises a graphical animation to indicate a process feature graphical element is to be selected.

17. The system of claim 1, wherein the display comprises a touchscreen.

18. A method for a medical treatment system comprising:
providing treatment apparatus comprising one or more pumps and one or more sensors for use in performing a treatment;
displaying a plurality of process feature graphical elements on a graphical user interface on a display to be used by a user to prepare a treatment, to perform a treatment, and to perform post-treatment processes, wherein the plurality of process feature graphical elements comprises at least one of a blood process feature graphical element corresponding to a blood circuit of the treatment apparatus, a dialysate process feature graphical element corresponding to a dialysate circuit of the treatment apparatus, an ultrafiltration process feature graphical element corresponding to one or more ultrafiltration processes, and a patient process feature graphical element representative of the patient and connection of the patient to a blood circuit of the treatment apparatus;
defining a normal workflow comprising a plurality of steps for the preparation of a treatment, the performance of the treatment, and the performance of post-treatment processes;
displaying one or more of a plurality of workflow affordances on the graphical user interface of the display to indicate to a user which of and how the plurality of process feature graphical elements are to be used to perform the plurality of steps of the normal workflow; and displaying a workflow deviation affordance on the graphical user interface in response to a user deviating from the normal workflow, wherein the workflow deviation affordance indicates which of and how the plurality of process feature graphical elements are to be used to return to the normal workflow.

19. The method of claim 18, wherein the method further comprises removing the one or more of the plurality of workflow affordances from the graphical user interface in response to display of the workflow deviation affordance.

20. The method of claim 18, wherein displaying a workflow deviation affordance on the graphical user interface in response to a user deviating from the normal workflow comprising displaying a workflow deviation affordance on the graphical user interface in response to the user deviating from the normal workflow using the plurality of process feature graphical elements.

21. The method of claim 18, wherein the normal workflow is at least partially defined by a prescription.

22. The method of claim 21, wherein the prescription comprises one or more of sodium settings, bicarbonate settings, anticoagulation settings, time, treatment modality, and ultrafiltration volume.

23. The method of claim 18, wherein the method further comprises displaying, after the display of workflow deviation affordance on the graphical user interface, an additional workflow deviation affordance on the graphical user interface in response to a user deviating further from the normal workflow using the plurality of process feature graphical elements, wherein the additional workflow deviation affordance indicates which of and how the plurality of process feature graphical elements are to be used to return to being on deviation away from the normal workflow.

24. The method of claim 23, wherein the method further comprises removing the workflow deviation affordance from the graphical user interface in response to display of the additional workflow deviation affordance.

25. The method of claim 18, wherein the method further comprises:
displaying an exceptions graphical element to allow a user to deviate from the normal workflow, and
displaying one or more deviations graphical elements in response to selection of the exceptions graphical element, wherein the one or more deviations graphical elements are selectable to initiate a deviation from the normal workflow.

26. The method of claim 25, wherein the one or more deviation graphical elements to deviate from the normal workflow comprise an end treatment graphical element to end an ongoing treatment when the treatment is being performed.

27. The method of claim 25, wherein the one or more deviation graphical elements to deviate from the normal workflow comprise an initiate disinfection graphical element to initiate disinfection of the treatment apparatus when a treatment is being prepared.

28. The method of claim 25, wherein the one or more deviation graphical elements to deviate from the normal workflow comprise a new treatment graphical element to initiate the preparation of a treatment without disinfecting the treatment apparatus when post-treatment processes are being performed.

29. The method of claim 18, wherein the method further comprises:
displaying a guide graphical element, and
displaying a guide area comprising information related to the next step of the plurality of steps of the normal workflow to be performed to continue the normal workflow in response to selection of the guide graphical element.

30. The method of claim 18, wherein the plurality of process feature graphical elements comprises:
the blood process feature graphical element corresponding to a blood circuit of the treatment apparatus;
the dialysate process feature graphical element corresponding to a dialysate circuit of the treatment apparatus; and
the ultrafiltration process feature graphical element corresponding to one or more ultrafiltration processes.

31. The method of claim 18, wherein the plurality of process feature graphical elements comprises the patient process feature graphical element representative of the patient and connection of the patient to a blood circuit of the treatment apparatus.

32. The method of claim 18, wherein the plurality of workflow affordances and the deviation workflow affordance comprises a graphical animation to indicate a direction that a process feature graphical element is to be moved.

33. The method of claim 18, the plurality of workflow affordances and the deviation workflow affordance comprises a graphical animation to indicate a process feature graphical element is to be selected.

\* \* \* \* \*